(12) United States Patent
Koenig et al.

(10) Patent No.: US 11,918,519 B2
(45) Date of Patent: Mar. 5, 2024

(54) SYSTEMS AND METHODS FOR MOVING A SURGICAL TABLE

(71) Applicant: Verb Surgical Inc., Santa Clara, CA (US)

(72) Inventors: Karen Shakespear Koenig, San Jose, CA (US); Pablo Garcia Kilroy, Menlo Park, CA (US); Richard W. Timm, Cincinnati, OH (US); Wayne Grout, San Francisco, CA (US); Robert T. Wiggers, Belmont, CA (US)

(73) Assignee: Verb Surgical Inc., Santa Clara, CA (US)

( * ) Notice: Subject to any disclaimer, the term of this patent is extended or adjusted under 35 U.S.C. 154(b) by 787 days.

(21) Appl. No.: 16/824,510

(22) Filed: Mar. 19, 2020

(65) Prior Publication Data
US 2021/0290466 A1    Sep. 23, 2021

(51) Int. Cl.
*A61G 13/10* (2006.01)
*A61B 34/35* (2016.01)
(Continued)

(52) U.S. Cl.
CPC ............ *A61G 13/104* (2013.01); *A61B 34/35* (2016.02); *A61G 1/0237* (2013.01);
(Continued)

(58) Field of Classification Search
CPC .... A61G 13/104; A61G 1/02; A61G 2203/10; A61G 1/0275; A61G 1/0237; A61G 2203/36; A61G 1/0268; A61G 7/018; A61G 1/0218; A61G 1/0293; A61G 2203/22; A61G 5/043; A61G 13/02; A61G 7/08; A61G 7/0528; A61G 1/0281; A61G 1/0225; B60B 33/063; B60B 2200/26;
(Continued)

(56) References Cited

U.S. PATENT DOCUMENTS 3,304,116 A    2/1967 Stryker
3,713,129 A    1/1973 Buchholz
(Continued)

FOREIGN PATENT DOCUMENTS

EP      4162913 A1    4/2023
WO    WO-2011030255 A1 *   3/2011   ........... A61B 6/4405
(Continued)

OTHER PUBLICATIONS

LaValle, Steven M., "Planning Algorithms", retrieved from the Internet <planning.cs.uiuc.edu/node659.html>, 2006, 3 pages.

*Primary Examiner* — Justin C Mikowski
*Assistant Examiner* — Madison Emanski
(74) *Attorney, Agent, or Firm* — Aikin & Gallant, LLP

(57) ABSTRACT

Several solutions are described for making it easier to move a surgical robotics patient table, either from rest or to turn it. The table has a base, a support, and a table top on which the patient is supported. A number of casters are mounted to a body of the base. In one case, controllable jacks lift the body to release the casters thereby allowing them to swivel to a desired orientation. In another case, a drive assembly is rotatably coupled to the body of the base and includes an electric drive motor and a drive wheel to drive the table across the floor. Other aspects are also described and claimed.

18 Claims, 17 Drawing Sheets

(51) Int. Cl.
  *A61G 1/02* (2006.01)
  *A61G 7/08* (2006.01)
  *B25J 5/00* (2006.01)
  *B25J 9/16* (2006.01)
  *B60B 19/00* (2006.01)
  *B60B 19/12* (2006.01)
  *B60B 33/00* (2006.01)
  *B60B 33/06* (2006.01)
  *A61B 17/29* (2006.01)
  *A61B 17/34* (2006.01)
  *A61B 34/00* (2016.01)
  *A61B 34/30* (2016.01)
  *A61G 7/05* (2006.01)

(52) U.S. Cl.
  CPC ............ *A61G 1/0275* (2013.01); *A61G 7/08* (2013.01); *B25J 5/007* (2013.01); *B25J 9/1689* (2013.01); *B60B 19/003* (2013.01); *B60B 33/063* (2013.01); *A61B 17/29* (2013.01); *A61B 17/3468* (2013.01); *A61B 34/25* (2016.02); *A61B 2034/301* (2016.02); *A61G 1/0225* (2013.01); *A61G 7/0528* (2016.11); *A61G 2203/10* (2013.01); *A61G 2203/36* (2013.01); *B60B 19/12* (2013.01); *B60B 33/0089* (2013.01); *B60B 2200/242* (2013.01); *B60B 2200/26* (2013.01)

(58) Field of Classification Search
  CPC ..... B60B 33/0089; B60B 33/04; B60B 33/06; B60B 2200/242; B60B 33/0092; B60B 19/003; B60B 19/12; B60L 2240/423; B60L 2240/463; G01L 5/00; G05D 2201/0206; A61B 34/30
  USPC ..... 5/600, 611, 618, 610, 613, 614, 11, 310, 5/510, 658, 661; 180/22, 54.1, 20; D24/183; 280/400; 296/20; 15/412, 15/319; 901/1
  See application file for complete search history.

(56) References Cited

U.S. PATENT DOCUMENTS

| | | | |
|---|---|---|---|
| 5,213,176 A * | 5/1993 | Oroku | G05D 1/0272 180/7.1 |
| 6,491,127 B1 | 12/2002 | Holmberg et al. | |
| 6,678,907 B1 | 1/2004 | Voelker et al. | |
| 10,478,359 B2 | 11/2019 | Kostic et al. | |
| 2008/0202837 A1* | 8/2008 | Macedo Ribeiro | A61G 5/046 180/236 |
| 2008/0289101 A1* | 11/2008 | Patterson | A61G 7/1032 5/81.1 HS |
| 2009/0299689 A1 | 12/2009 | Stubben | |
| 2011/0087416 A1* | 4/2011 | Patmore | A61G 1/0287 180/19.1 |
| 2012/0185095 A1* | 7/2012 | Rosenstein | G05D 1/0227 901/1 |
| 2015/0216746 A1* | 8/2015 | Dirauf | B62D 15/00 701/25 |
| 2017/0281440 A1* | 10/2017 | Puvogel | A61G 7/0527 |
| 2018/0147104 A1 | 5/2018 | Timm et al. | |
| 2018/0250178 A1* | 9/2018 | Paul | A61G 7/0528 |
| 2019/0160865 A1* | 5/2019 | Bhat | B60B 19/003 |
| 2021/0401654 A1 | 12/2021 | Hoel et al. | |
| 2022/0117818 A1 | 4/2022 | Obert et al. | |

FOREIGN PATENT DOCUMENTS

| | | | | |
|---|---|---|---|---|
| WO | WO-2017001497 A1 * | 1/2017 | ........... | A61G 1/0275 |
| WO | WO-2018154750 A1 * | 8/2018 | ............ | A61G 13/02 |

* cited by examiner

SYSTEMS AND METHODS FOR MOVING A SURGICAL TABLE

FIELD

This disclosure relates generally to the field of surgery, and, more particularly, to surgical tables for supporting patients in a robotics surgery operating environment.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. MIS provides multiple benefits, such as reduced patient scarring, less patient pain, shorter patient recovery periods, and lower medical treatment costs associated with patient recovery.

MIS may be performed with robotic systems that include multiple robotic arms at the distal ends of which are attached various surgical instruments or tools. The arms have several motorized or actuated joints that are controlled by a digital control system which responds to commands given by a remote operator (surgeon.) The robotic arms are mounted to a surgical table that also supports the patient, in such a way that enables the various robotic arms to be moved or re-arranged to yield a suitable setup position that allows physical access to the patient by a table side operator, reduces the likelihood of collisions between arms, and reduces the distance that the surgical tools (which are attached to the robotic arms) need to travel, to reach the surgical site in the patient. The surgical table should also be moveable (also referred to here as mobile or maneuverable), e.g., repositioning during surgery, taken from one operating environment to another (e.g., different rooms), and during storage.

SUMMARY

In surgical procedures, surgical tables are provided within the operating environment to support a patient in a stable and accessible position for surgical procedures. In order to provide a versatile platform for supporting the patient, the surgical table can be provided with rollers or casters such that the surgical table can be moved within the surgical environment, between multiple surgical environments, can transport the patient to and from the surgical environment, and can additionally be delivered and retrieved from storage.

In addition to supporting the patient, the surgical table can be configured to support various equipment related to a surgical procedure. This may include equipment associated with the patient such as respirators, intravenous fluid drips, etc., as well as surgical robotic arms, associated arm mounting and actuating equipment, monitors, and other equipment to be used in the course of a surgical procedure that can be mounted or supported on the surgical table.

The aforementioned equipment, in addition to the weight of the patient and the table itself, can produce a total load (i.e., weight) that can require a substantial force to be exerted by an operator in order to begin rolling the table or changing its direction. Such high force levels, which can be as much as 500 Newtons or more, mean that several human operators are needed to move the table, the risk of injury to such operators due to overexertion is increased, and fine control over the orientation and speed of the table is not easy, which as a whole reduce overall efficiency during surgical procedures.

In this regard, systems and methods of assisting the driving (forward or backward) and turning of a surgical table are needed to reduce or obviate the challenges presented when manually forcing the surgical table to move. For example, motors, stored energy devices, and manual actuators can be provided with the surgical table to provide such assistance in driving and turning surgical tables.

Generally, in one aspect, a surgical robotic system can include a surgical table for supporting a patient. The table can include a base, a support or pedestal extending upwardly from the base, and a table top on which the patient lies and that could also support equipment. The base, support, and table top can be adjustable or articulable with respect to one another, for example, to position the patient at a desired height or orientation during a surgical procedure.

The table can be provided in a wheeled or rolling configuration in which several casters are rotatably mounted to the body of the base and lie on the floor. The casters thus define a surface-engaging end of the table that contacts a floor below the table. The casters may be part of a separately formed support assembly that is coupled to the body of the base.

Also coupled to the body of the table base is a drive assembly with at least one electric drive motor and at least one drive wheel. The drive motor is in mechanical communication with at least one drive wheel to drive the table along the floor (e.g., in a straight line or in the direction or orientation of the drive wheel) upon signaling, for example, by a processor of an operator console. The drive motor can drive the drive wheel through a mechanical transmission such as a gearbox.

The drive assembly can include a housing that is rotatably mounted to the body of the table base via a bearing, e.g., a roller element bearing that enables the housing to freely rotate relative to the body, about a vertical axis of the drive assembly in both clockwise and counterclockwise directions and spanning 360 degrees. The housing can rotate "freely" when it is unconstrained except by the practical (internal or inherent) friction of the bearing. The drive assembly can support the at least one drive wheel such that upon rotation or turning of the drive assembly about its vertical axis, the at least one drive wheel rotates as one with the housing, with respect to the body of the table base. In one variation, an electric rotation motor can be mechanically coupled to the drive assembly housing, for example, with a worm and spur or bevel gear arrangement, such that the rotation motor drives the drive assembly housing (and the supported drive wheels) to rotate with respect to the table base until it has reached a selection direction or orientation. The drive assembly may also be part of the separately formed support assembly (that is then coupled to the body of the base.)

In one variation, the drive assembly includes a first drive wheel driven by a first drive motor and a second drive wheel driven by a second drive motor. The first drive wheel and the second drive wheel can be mechanically coupled with the respective first drive motor and the second drive motor so as to be differentially driven. For example, the first drive wheel and the second drive wheel can be driven in opposite rotational directions so as to exert a torque on the drive assembly housing that causes the drive assembly housing to rotate with respect to the body of the table base to orient the drive wheels in a selected orientation for steering the table.

Jacks may be added that can be actuated to extend downwardly from the body of the base against the floor, to lift, raise or suspend one or more portions of the table above the floor. The jacks may be mounted to the support assembly and formed separately (along with the casters). The jacks can be signaled, for example, by a processor of the operator console to advance or retract. In one aspect, the jacks are actuated to advance until they have raised a caster off the floor which can then be free to rotate. In other words, one or more jacks can be selectively actuated to enable a selected caster to rotate or swivel itself toward a selected orientation. In another variation, the jacks advance until they have raised the drive wheel of the drive assembly above the floor, and so the drive assembly now being free from contact with the floor can freely rotate to a selected orientation due to its asymmetrical weight distribution being acted upon by gravity (so that a center of mass of the drive assembly rotates toward the selected orientation.) In addition to or instead of the jacks, one or more actuators 161 can be coupled to drive the casters vertically, so that one or more of the casters advances with respect to the body of the base 150 thereby raising the first drive wheel off the floor.

Each caster of the table can include a caster wheel supported on a caster frame. In one variation, one or more of the caster wheels can be mechanically coupled with a drive motor such that the respective caster wheels are the drive wheels that drive the table forward and backward (on the floor.) For example, the table can include four casters, and the caster wheels of at least a pair of diagonally opposite casters can be mechanically coupled with a drive motor to drive the table along the floor (in the steering direction of the caster wheels.) In another variation, each of all four caster wheels can be mechanically coupled with (and driven by) its respective drive motor.

In still another variation, an electric rotation motor can be mechanically coupled to the respective caster, for example, with a worm and spur or bevel gear arrangement, such that the rotation motor turns or rotates (swivels) the caster about a vertical axis of the caster (with respect to the table base.)

In another variation, each caster includes a spherical wheel that may be retained on a frame of the caster, so that the respective spherical wheel is free to rotate along the floor in three rotational degrees of freedom (DOFs): X-axis rotation, Y-axis rotation, and Z-axis rotation. In one variation, the spherical wheel can be formed from a metallic material.

In still another aspect of the disclosure, a rolling or wheeled surgical table is disclosed that can include a base and a table top supported on the base that can support a patient or other equipment. Two or more casters are rotatably mounted to the body of the base (so that each caster can swivel relative to the body) and support the table on the floor. A vibration motor is mechanically coupled to a portion of the surgical table to induce one or more vibrations across the surgical table. Such vibrations cause one or more of the casters to oscillate intermittently, so as to have momentary and intermittent contact with the floor. During such oscillations, one or more of the casters is freed from contact with the floor so as to reduce or remove friction, between the respective casters and the floor, thereby making it easier to push or pull the table at the same time to roll it along the floor.

In yet another aspect of the disclosure, a manual actuator is coupled to the wheeled surgical table (having a plurality of casters rotatably mounted to the body of the base of the table). The manual actuator is configured to redirect or amplify an input force exerted by a hand or foot of an operator, or in other words convert the input force applied by the operator, into an impulse load that is capable of rolling the surgical table across the floor. In one variation, the manual actuator can be one or more kinematic straps that are coupled to the table. The kinematic straps can be reconfigurable such that, upon pulling by an operator, the kinematic straps elongate from a first length to a second, longer length. In this regard, the kinematic straps can be elastomers or other elastic material. In another variation, the manual actuator can be a drive spring that is in mechanical communication with one or more of the casters of the table, for example, through a direct coupling or a mechanical transmission. The drive spring can be a helically-wound torsion spring such that the drive spring is reconfigurable between a resting configuration and an actuated or twisted configuration upon receiving an applied torque. The applied torque can be provided by an operator, for example, by pulling the table to thereby rotate one or more of the casters which in turn twists the drive spring. Or can be provided by an operator through another mechanism such as a hand/foot operated crank or lever. The drive spring is biased to return to the resting configuration, such that upon actuation the drive spring provides a torque to one or more of the casters to roll the table along the floor. In still another variation, the manual actuator can comprise a drive station in mechanical communication with a portion of the surgical table. Such a drive station can be anchored to the floor or to another stationary structure such as a wall, frame, etc. The drive station includes a mechanical input interface, for example, a hand or foot operated crank or lever (e.g., a foot pedal, etc.), that is coupled through a mechanical linkage to an output finger or other actuator that is extensible from the drive station upon actuation of the mechanical input interface. In one variation, the mechanical input interface can be a foot pedal that is forcibly depressed by an operator to cause the output finger to extend from the drive station to impart a force to the table and cause the table to roll across the floor.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
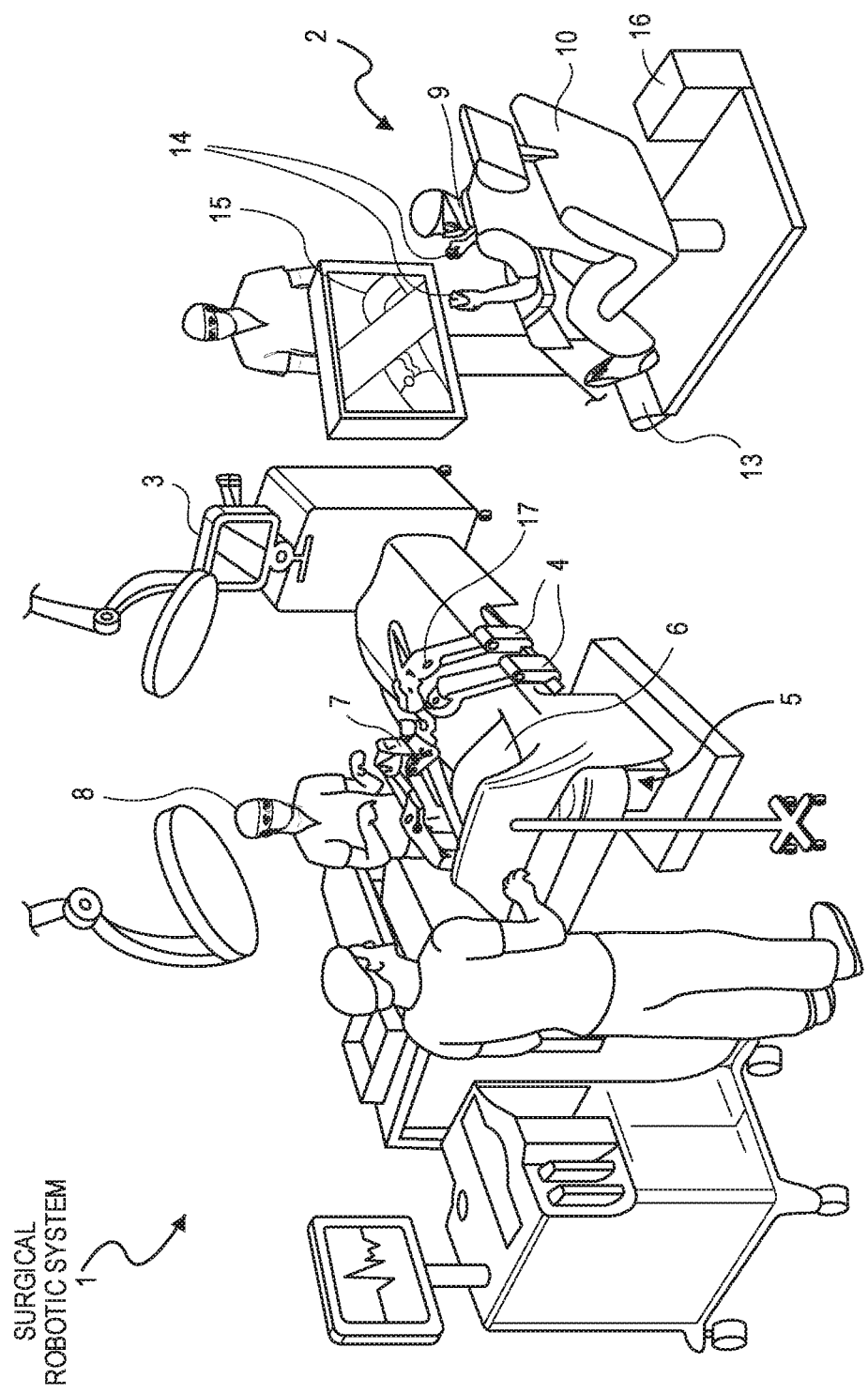
FIG. 1 is an overview schematic of an operating room arrangement with a surgical robotic system.

Referring to FIG. 1, this is a pictorial view of an example surgical robotic system 1 in an operating arena. It will be understood that the system 1 can be configured as a general surgical system that includes minimal robotic surgical equipment or does not include robotic surgical equipment. The system 1 includes a user console 2, a control tower 3, and one or more surgical robotic arms 4 that are coupled to a surgical robotic platform generically referred to here as a table 5, e.g., a bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted on a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, a bedside operator 8 may also operate the system 1 in an "over the bed" or table side mode, in which the bedside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), prior to initiating surgery with the surgical robotic system 1, the surgical team can perform the preoperative setup. During the preoperative setup, the main components of the surgical robotic system (table 5 and robotic arms 4, control tower 3, and user console 2) are positioned in the operating room, connected, and powered on. The table 5 and robotic arms 4 may be in a fully-stowed configuration with the arms 4 under the table 5 for storage and/or transportation purposes. The surgical team can extend the arms 4 from their stowed position for sterile draping, e.g., covering one or more portions of the system 1, such as portions of the arms 4, with a sterile barrier to minimize, inhibit, or prevent the transmission of pathogens. After draping, the arms 4 can be partially retracted until needed for use. A number of conventional laparoscopic steps may need to be performed including trocar placement and insufflation. For example, each trocar can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars or other tools or equipment.

In one embodiment, the remote operator 9 holds and moves the UID 14 to provide an input command to drive one or more robotic arm actuators 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control motions of the robotic arm actuators 17. The robotic system 1 may use control signals derived from the spatial state signals, to control proportional motion of the actuators 17. In one embodiment, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the table 5 and the user console 2 may be through a control tower 3, which may translate user commands that are received from the user console 2 (and more particularly from the console computer system 16) into robotic control commands that are transmitted to the arms 4 on the table 5. The control tower 3 may also transmit status and feedback from the arms and the table back to the user console 2, as well as control various functions of the table 5, such as motors and actuators for tilting and translating the table. The communication connections between the table 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

As described above, to create a port for enabling introduction of a surgical instrument into the patient 6, a trocar assembly may be at least partially inserted into the patient through an incision or entry point in the patient (e.g., in the abdominal wall). The trocar assembly may include a cannula or trocar, an obturator, and/or a seal. In some variations, the trocar assembly can include an obturator such as a needle with a sharpened tip for penetrating through a patient's skin. The obturator may be disposed within the lumen of the trocar when being inserted into the patient 6, and then removed from the trocar such that a surgical instrument may be inserted through the lumen of the trocar. Once positioned within the body of the patient 6, the trocar may provide a channel for accessing a body cavity or other site within the patient 6, for example, such that one or more surgical instruments or tools can be inserted into a body cavity of the patient 6, as described further herein.

Surgical Tables for Surgical Robotic Systems

As described above, at least the robotic arms 4 and the patient 6 are supported on the surgical table 5 such that a significant amount of force needs to be applied to the table 5 to overcome inertia and initiate rolling of the table 5 across a ground surface or floor, even in the case where the table 5 is provided with wheels or casters for rolling the table 5. In particular, such forces on the table 5 must overcome at least static friction (i.e., the product of the force of the floor on the table 5 in response to the weight of the table 5, and a coefficient of static friction that is determined by the properties of the materials of the floor and the wheels of the table 5 that are contact with the floor) to begin linear translation of the table 5 across the floor. At that point forces due to dynamic or rolling friction become the minimum level of force on the table 5 needed to continue movement or to accelerate along the floor. Additional forces can be needed to turn or reorient the table 5 in a desired direction, for example, to rotate or reorient casters and wheels to a desired orientation.

In the case of manual manipulation or forcing of the table 5, e.g., an operator physically exerts the required forces for moving the table 5, such forces can be burdensome and are likely to require several operators to move the table 5 or they may increase the risk of injury to the operators, making it difficult to effect fine control over the orientation and speed of the table 5. Accordingly, it is desirable to provide systems that provide forces to the table 5 that assist or obviate the need for an operator's manual exertion on the table 5, and, in particular, forces that can make it easier to initiate movement of the table across the floor or to change the orientation of the table 5.

Figure 2:
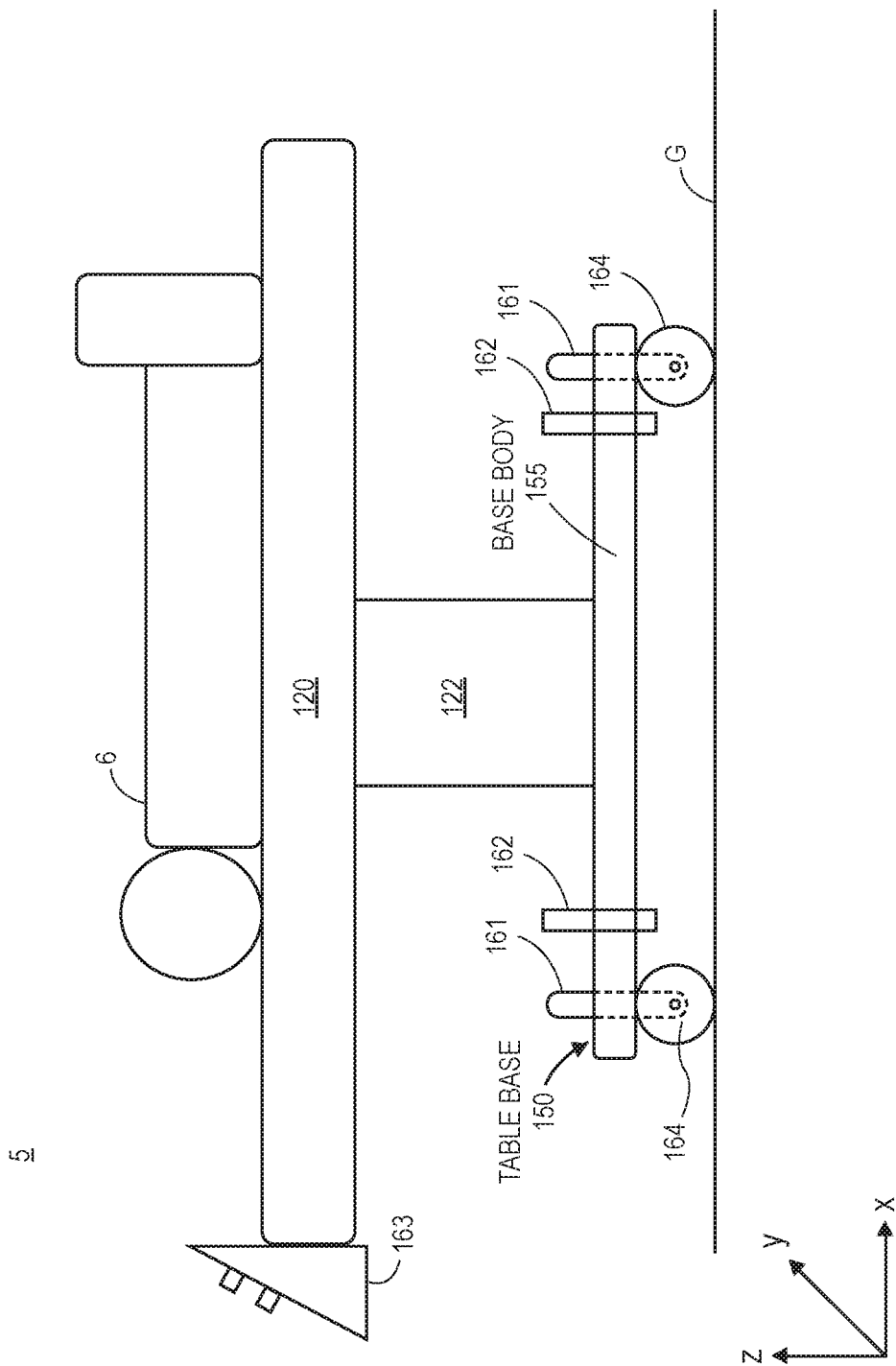
FIG. 2 is a schematic of a surgical table according to one aspect of the disclosure.
Figure 3:
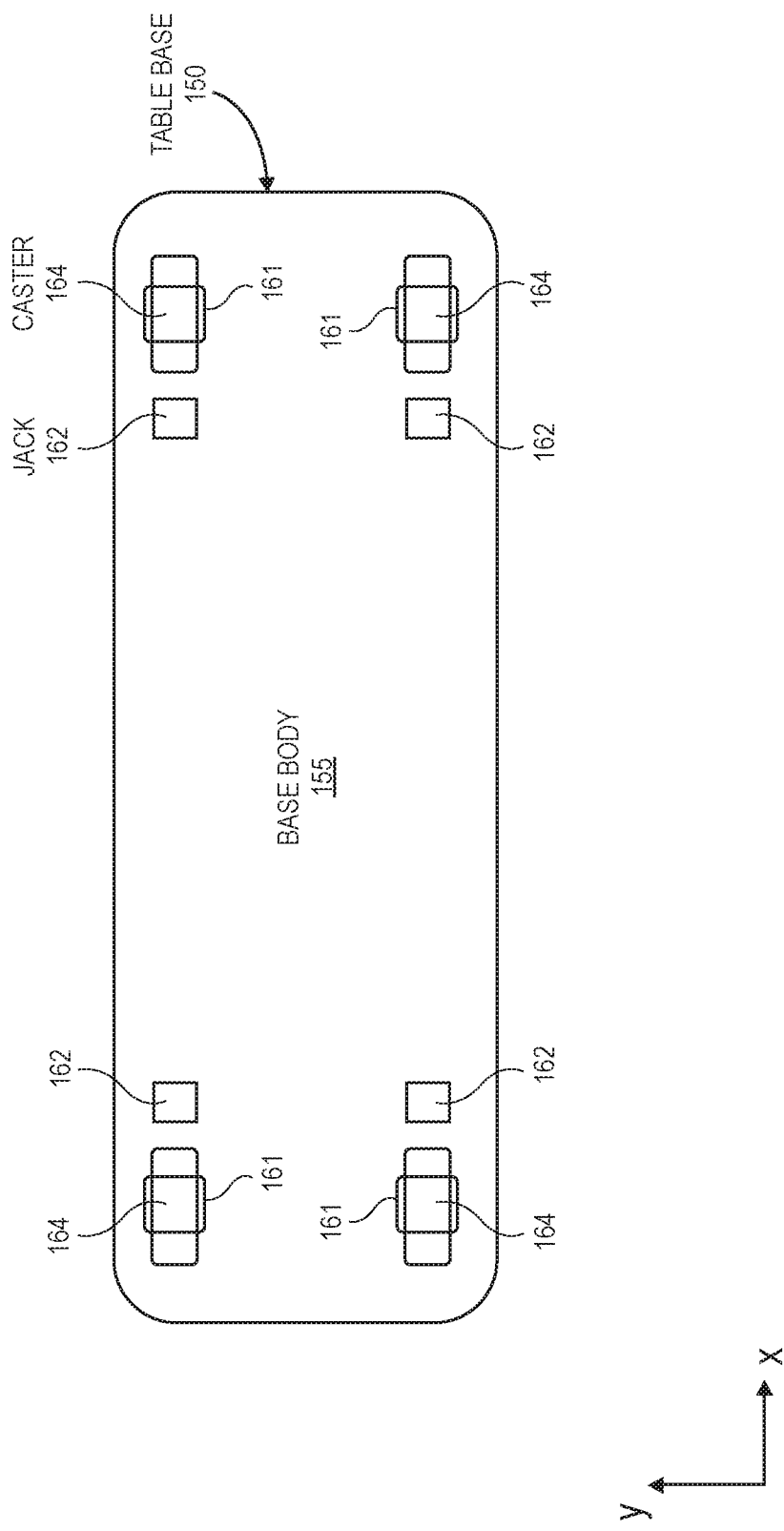
FIG. 3 is another schematic view of the surgical table of FIG. 2.

Referring to FIG. 2 and FIG. 3, an example of the surgical table 5 that can form part of the surgical system 1 according to one aspect of the disclosure is schematically illustrated. The table 5 includes a table top 120, a table top support 122 and a table base 150. The table top 120 has an upper surface on which the patient 6 can be disposed during a surgical procedure, for example as shown in FIG. 1. The table top 120 is disposed on the table top support 122, which can be, for example, a pedestal or column, at a suitable height above a ground or floor G on which the table 5 rests. The table top support 122 may provide for movement of the table top 120 in a desired number of degrees of freedom (DOF), such as translation in the Z-axis (height above the floor), X axis (along the longitudinal axis or length dimension of the table top 120), and/or Y-axis (along the lateral axis or width dimension of the table top 120), and/or rotation about the Z-, Y-, and/or X-axis. The table top 120 may also include multiple sections that are movable relative to each other along or about any suitable axes, e.g., separate sections for each of the torso, one or both legs, and/or one or both arms, and a head support section. Movement of the table top 120 or its constituent sections may be affected via manual force by an operator, driven by motors or actuators, controlled remotely, or through any other suitable means, e.g., through hydraulic lifts.

The support 122 for the table top 120 may be mounted to the base 150. In some embodiments, the height of the support 122 can be adjusted, which together with, for example, the motion (e.g., longitudinal or lateral motion) of the table top 120, can allow for the table top 120 to be positioned at a desired surgical site at a certain height above the floor G (e.g., to allow surgeon or other medical professional access) and a certain distance from the support 122.

The base 150 is configured to support a surgical table load, and to monitor and/or adjust distribution of a total load (the table load together with the weight of the base 150) to the floor G. The table load is a collective load including loads from various components of the surgical table 5, such as, for example, the table top 120, the support 122, and associated components that can be mounted to the surgical table 5 such as robotic arms 4, batteries (not shown), table-arm adapters and mounting systems, as well as the patient 6. In one configuration of the table 5, the total load can be from about 800 kg-1000 kg or more (about 809 N to about 9,810 N by weight), and the force required to initiate rolling of the table 100 can be about 500 N or more.

Referring to the top view in FIG. 3 (with the table top support 122 omitted), the base 150 includes a base body 155 to which are attached several casters 164 (four are shown) that transmit the total load from the base body 155 to the surface the floor G below the table 5. The floor G can be a generally flat supporting surface that is suitable for a surgery operating environment, and can be formed from materials such as polymeric materials (e.g., rubber matting, foam, etc.) and composite materials (e.g., tile, wood-thermoplastic composite material, linoleum, etc.). While the floor G is illustrated as generally flat, it will be understood that the floor G can include one or more uneven sections, discontinuities, or surface irregularities, for example, due to dirt or debris, seams, equipment or cables, etc.

As shown in the top view of FIG. 3, the table base 150 can be fitted with one or more jacks 162 (in the example shown, four) that can be driven downward or advanced below the base body 155 until it pushes against the floor G and thereby raises the base 150 above the floor G. In another scenario, the jacks 162 can be driven downward until they push against the floor G but do not have to raise the table, and instead exert a 'seating' force to the floor and then are locked in position. The purpose of this is to increase stability of the table 5 with 4 point contact, in cases of an uneven floor, such that as the center of gravity of the table moves (in longitudinal, lateral, pitch, or tilt motions) the table base 150 remains in solid connection wish the floor. Each jack 162 is also retractable relative to the base body 155, e.g., having a ram that slides up when the jack is retracting, and down when the jack is advancing, with respect to the base body 155. In this regard, the jacks 162 can be advanced and/or retracted with a suitable actuator such as an electrical motor or actuator, a hydraulic lift system, or can be at least partially actuated by force exerted by an operator via a mechanical linkage such as a crank or lever that can be engaged by a hand or foot of an operator. The jack 162 can be signaled from a table operator console 163 that includes one or more user control interface elements, e.g., buttons, knobs sliders, switches, levers, touchscreens, etc., that are in electronic communication with one or more actuators of the jacks 162, to advance or retract one or more of the jacks 162. In one variation, actuation of the jacks 162 can be signaled by a controller or programmed processor that is incorporated into another portion of the surgical system 1, for example, the control tower 3.

The jacks 162 can be signaled to actuate from the operator console 163 to forcibly extend downwardly from the base body 155 and raise the base above the floor G, for example, to raise or tilt the patient 6 to a desired position and orientation, to provide some access space below one or more portions of the base 150 (see FIG. 2), or to overcome obstacles such as cables, doorjambs, surgical equipment, etc. Similarly, the table 5 can also be lowered by actuating the jacks 162 from the operator console 163 to retract to thereby return the base to a level, lowered position against the floor G.

As also shown in FIG. 3, the table base 150 can be fitted with one or more casters 164 that are in contact with the floor G and support the weight the table 5 against the floor G (when the jacks 162 have been fully retracted.) The table 5 is thus provided with a wheeled or rolling configuration. In the illustrated variation, four casters 164 are provided near respective corners of the base body 155, though it will be understood that a different number or arrangement of casters 164 can be provided without departing from the disclosure. The casters 164 may be part of a separately constructed support assembly that is then coupled to the base body 155.

Figure 8:
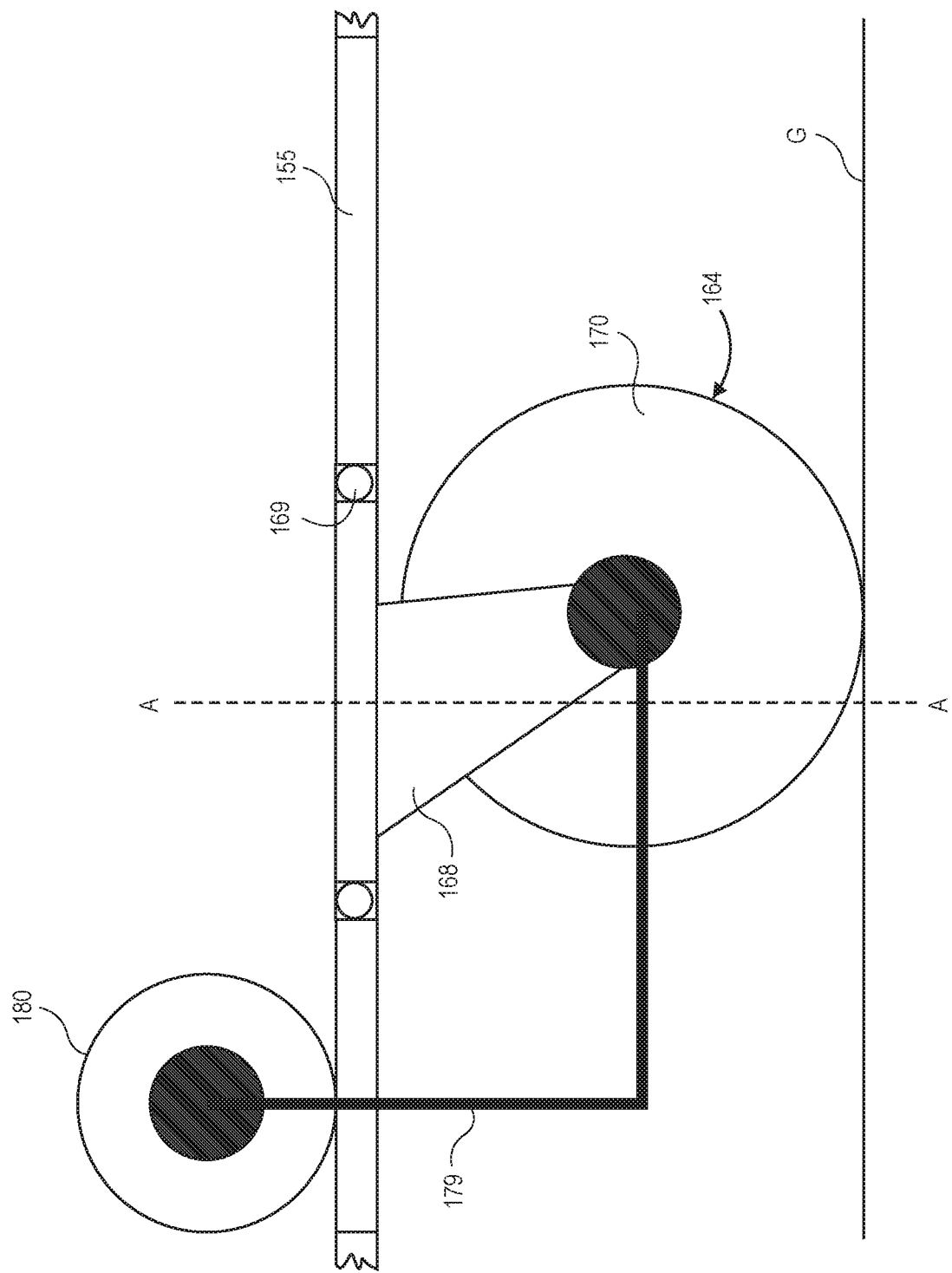

In one variation, as shown in the side view of FIG. 8, the caster 164 can include a horn or frame 168 that is rotatably coupled to the base body 155. The rotatable coupling may be achieved using, for example, by mounting the frame 168 to a bearing 169 that is disposed between the frame and the base body 155. The bearing 169 can be, for example, a rotatable-element bearing having an outer ring that is affixed to the base body and is stationary relative to an inner ring to which the frame 168 is affixed, and allows the frame to swivel freely 360 degrees. Other bearing configurations are possible. A caster wheel 170 is supported on the frame 168, for example, via an axle or spindle extending between opposed portions of the frame 168. The caster wheel 170 can be configured to frictionally engage the floor G, for example, with a rubber or other suitable gripping surface or coating applied to its perimeter. As shown, the frame 168 of the caster 164 extends away from the base body 155 to support the caster wheel 170 at a position that is offset from an axis of rotation A of the caster 164, such that the caster wheel 170 is configured to swivel about the axis A. While the caster 164 is illustrated as including a single caster wheel 170, it will be understood that the caster 164 could include a pair of caster wheels 170.

Figure 4:
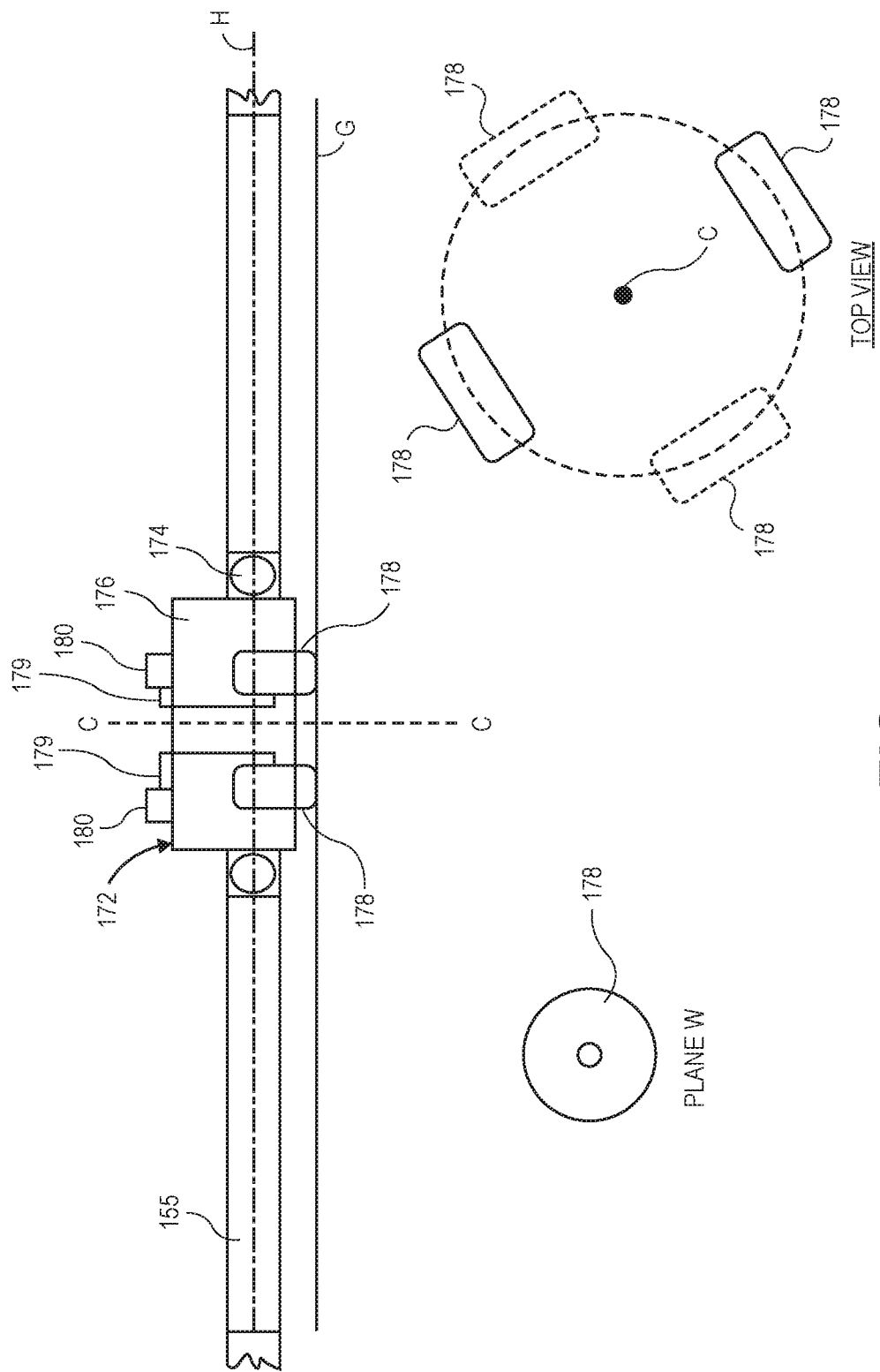
FIGS. 4-17 are schematic views of variations of the surgical table of FIGS. 2 and 3 according to various aspects of the disclosure.

In one aspect of the disclosure, the casters 164 can be passive elements upon which the table 5 can roll when acted upon by an external force. Referring now to FIG. 4, to reduce the physical effort needed by an operator for moving the table 5 in such a configuration, a drive assembly 172 can be provided that delivers an impulse load (e.g., a force that imparts a change in momentum) to the table 5, making it easier for the table 5 to move in different directions. As shown in FIG. 4, the drive assembly 172 is rotatably mounted to a horizontal portion of the base body 155 of the table 5 to freely rotate about an axis C. Such a free rotational coupling of the drive assembly 172 can be achieved using a bearing 174 that is in circumferential engagement with and between a housing 176 of the drive assembly 172 and the horizontal portion of the base body 155. The bearing 174 can be, for example, a rotatable-element bearing having an outer ring that is affixed to the base body and that is stationary relative to an inner ring to which the housing 176 is affixed. Other bearing configurations are possible. The bearing 174 supports free rotation of the housing 176 about the axis C, relative to the base body 155. The axis C may be defined to be at the center of, and perpendicular to a plane H defined by the bearing 174 in the base body 155.

The drive assembly housing 176 also supports a pair of independently-rotatable freely rotating drive wheels 178 both of which are in contact with the floor G and will bear some portion of the table load. The drive wheels 178 may be located in respective recesses having horizontally oriented axles or spindles. Each drive wheel 178 is mounted so as to revolve with its respective rotating, horizontal axle, wherein the first axle is mounted to the housing such that the first drive wheel is in contact with the floor when the casters are resting on the floor. In such an arrangement, the drive wheels 178 protrude below the housing 176 to be in contact with the floor G, and frictional contact between the drive wheels 178 and the floor G may be provided through a rubber or other suitable surface configuration or coating of the wheels 178. A different number or arrangement of the drive wheels 178 can be provided without departing from the disclosure.

The drive assembly 172 is thus provided in a compact or puck-like unit that can easily be coupled with the base body 155. The drive assembly 172 can be positioned relative to the base body 155 such that the drive assembly 172 is not a fully load-bearing member, i.e., so that a greater proportion of the table load is shared by the casters 164 than by the drive assembly 172. While the drive assembly 172 is shown to be vertically fixed to the table base 150, in variations, the drive assembly 172 can be movably mounted to the table base 150 in a vertical direction, e.g., through an electric motor or actuator or hydraulic lift. In this regard, the drive assembly 172 can be provided in an advancing and retractable arrangement with regard to the base body 155.

Several aspects are now described for adapting and using the drive assembly 172 to make it easier to turn the table 5 in a different direction, either from rest or while the table is already moving. In one approach, referring still to FIG. 4, an electric motor 180 is provided in mechanical communication with each wheel 178, and in particular in mechanical communication with the respective axle to drive the axle and thereby drive the base along the floor. The electric motor 180 is in electrical communication with a power source, for example, a battery, generator, or electrical power grid, and is in mechanical communication with a respective drive wheel 178 via a mechanical transmission 179. The transmission 179 can include a drive shaft that is output from a gearbox or gearing assembly that is actuated by rotation of the respective electric motor 180. The latter can be signaled from the operator console 163. Such gearboxes and gearing assemblies can include, for example, spur gears, worm gears, bevel gears, planetary gears, harmonic drives, etc. The electric motor 180 can be for example, a brushless DC motor or an AC motor, and can have features that facilitate the driving of the table 5 as described above, for example, slip rings, sensors, etc. While a pair of driving motors 180 is shown each separately driving its respective wheel 178, it will be understood that any combination of one or more wheels 178 driven by one or more motors 180 is possible.

The turning or reorienting of the table 5 about the Z-axis, i.e., turning the table 5 toward a left-hand or right-hand direction, generally requires additional forces, e.g., torque, to be exerted on the table 5 to overcome the moment of inertia of the casters 164 due to the offset of the caster wheels 170 from the respective axis A, as well as the frictional forces generated between the caster wheels 170 and the floor G, also known as forces required to overcome the effect of "caster flip" and thereby turn or swivel the caster into a different, desired direction. There is a need here to provide the drive assembly 172 with the capability to affect rotation of the table 5 about the Z-axis so that the table can be turned, for example, to avoid obstacles, to navigate hallways or doorways, or otherwise achieve a desired positioning of the table 5 such as sideways movement.

The processor can detect an indication to move the table, for example as a manual input by the operator pressing a button or pulling a handle of the operator console 163 indicating that the table should be turned. The processor can alternatively detect an indication to move the table, by detecting the torque produced when one or more of the casters 164 begins to swivel (because the wheel 178 of the caster is off axis from the swivel bearing of the caster and is in contact with the floor while bearing part of the table load) when a side force is applied by the operator onto the table 5.

Still referring to FIG. 4, in one aspect, the two wheels 178 may be mounted to the housing 176 so as to be co-axial with each other as shown. A programmed processor in the operator console may detect an indication to move the table, e.g., sensing a button being pressed by the operator or sensing a force applied by the operator to the table 5. The operator console signals or activates the electric motors 180 to rotate, such that they impart a rotational force on the respective wheels 178 to drive the two wheels 178 in opposite directions simultaneously. The motors 180 can be separately controlled from the operator console 163 to differentially drive the respective drive wheels 178 to exert a torque on the drive assembly housing 176 to cause rotation thereof about the rotation axis C extending through the drive assembly 172. In other words, the drive assembly 172 can be reoriented through selective and differential operation of the motors 180 from the operator console 163 that results in the two wheels 178 being driven to revolve in opposite directions simultaneously. If one wheel 178 is driven forwardly by its motor 180 and the other wheel 178 is driven rearward by its motor 180 simultaneously, the drive assembly 172 experiences a torque that rotates the drive assembly housing 176 circumferentially along the bearing 174 about the axis C. This in turn changes the location of the two wheels 178 along the circle—see the illustration in FIG. 4 showing an example where the direction has been changed by ninety degrees.

In one aspect, the programmed processor of the operator console selects a direction to which the table is to be turned, in accordance with the detected indication to move the table. For example, a control knob or joystick may be manually turned or pushed by the operator to the selected direction, indicating a desire that the table turn or change its orientation. The programmed processor will then differentially drive the first and second drive wheels as described above, until the housing of the drive assembly 172 is rotated to match the selected direction.

Once the drive assembly 172 has been placed in the selected orientation, e.g., with the two wheels 178 aligned with or parallel to a desired table direction in which to turn the table 5, the motors 180 can then together be signaled from the operator console 163 to drive the table 5 in the selected direction such that the motors 180 provide or assist an operator in providing a torque to the table sufficient to overcome caster flip, to turn the table towards the desired direction (the selected orientation of the drive assembly 172.) In this regard, each wheel 178 would now be driven to rotate in the same direction at the same speed, or perhaps at different speeds so as to exert a measure of fine control on movement of the table. It will be understood that the aforementioned selective orientation change of the drive assembly 172 can be performed while the base is stationary or while the base is in motion.

Once the base (or the table 5) has been turned and has reached the desired orientation or angle, the operator may signal the motors 180 of the drive assembly 172 to drive both wheels 178 simultaneously and in the same direction, e.g., at the same speed. The wheels 178 will thus grip the floor G to impart a driving force on the table that releases from rest, or continues to move (roll) the table in a straight line. The motors 180 can be signaled to drive the wheels 178 together, e.g., simultaneously at the same speed, in a clockwise or counterclockwise rotation, to release or move the table forward or backward across the floor G.

Figure 5:
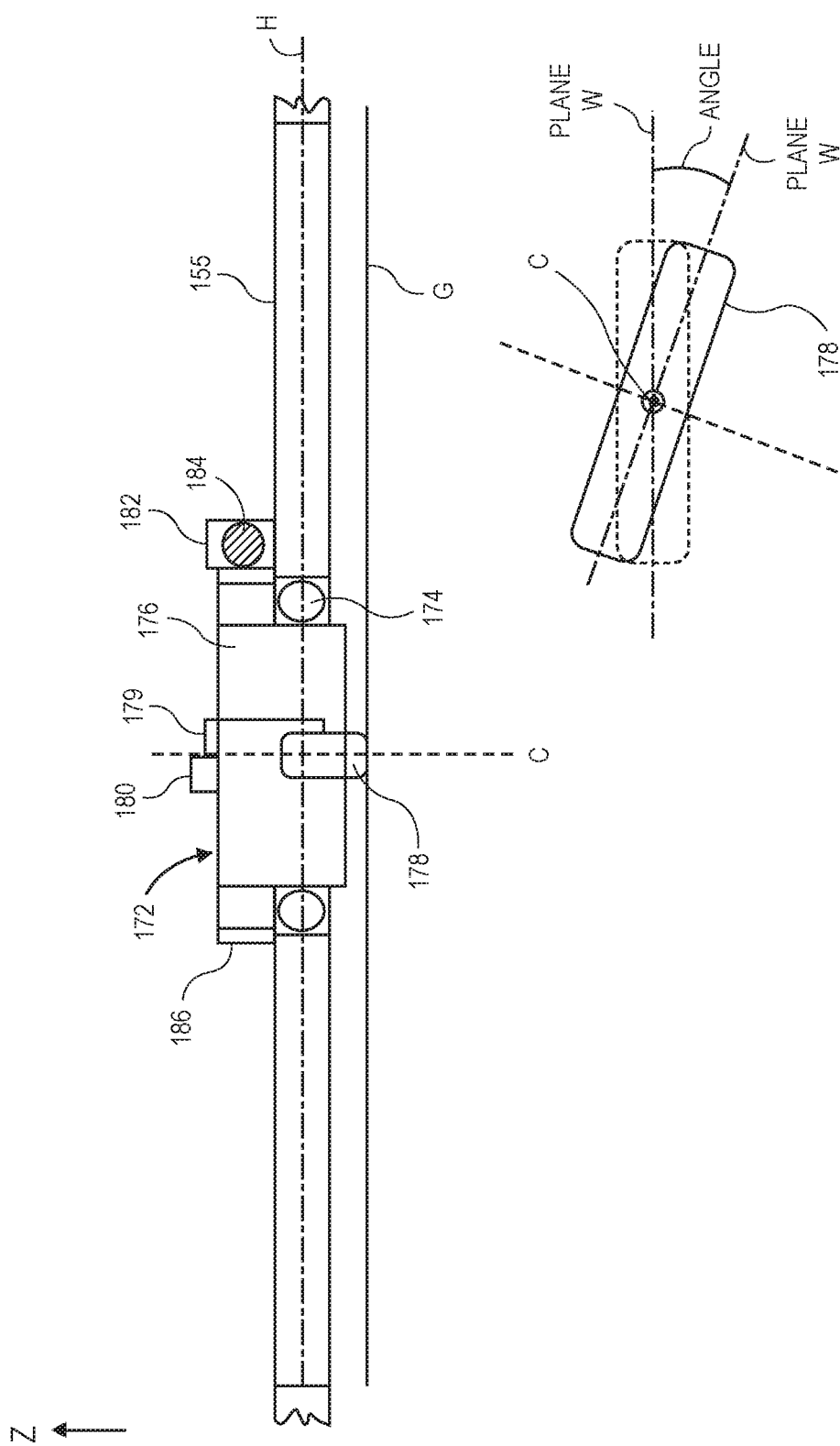

Referring now to FIG. 5, in this variation the drive assembly 172 is provided not only with the motor 180 to drive the drive wheel 178 so that it revolves about its axle, as described above in connection with FIG. 4, but also an additional electric motor 182 is provided on the base body 155 that is mechanically coupled to rotate the drive assembly housing 176 relative to the base body 155 (in a horizontal plane H through the base body 155), to affect rotation of the drive assembly 172 about the vertical axis C. The motor 182 is electrically coupled with a power source and the operator console 163 and can be in mechanical communication with a gearbox or transmission such that rotation of its output shaft is converted into rotational motion of the drive assembly housing 176 about the axis C. For example, in one variation, upon signaling from the operator console 163, the output shaft of the motor 182 is actuated to drive a worm gear 184 which is positioned to mesh with and drive a spur gear 186 (or a circumferential arrangement of surface features of the drive assembly housing 176) to rotate the drive member housing 176 along the bearing 174 and about the axis C, toward a desired orientation. Once the desired orientation has been reached, where the wheel 178 rotates with the housing 176 about the axis C until a desired angle is reached (as shown in the illustration in FIG. 5), the operator (via the operator console 163) may signal the motor 180 to drive the wheel 178. The latter will thus grip the floor G and thereby imparts force to turn the table 5 in the selected direction, which will flip the casters 164 (if needed), as described above. Here it again, it should be noted that in FIG. 5 a single wheel 178 is shown that is in mechanical communication with a single motor 180, but that it will be understood that in general any suitable combination of one or more wheels 178 and one or more motors 180 that drive them may be used to turn the table 5.

Figure 6:
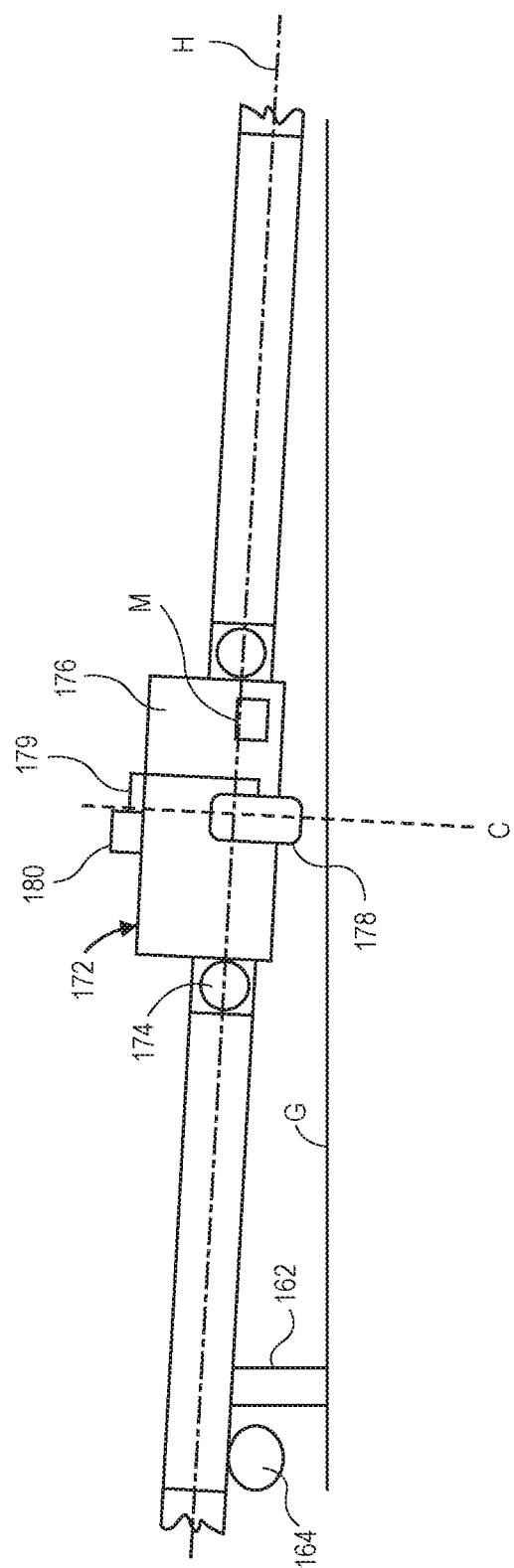

Turning to FIG. 6, in another aspect of the disclosure here, the drive assembly 172 can be turned "passively" about its axis C, rather being actively driven as in the embodiments of FIG. 4 and FIG. 5. In FIG. 6, the drive assembly 172 is provided with an asymmetrical weight distribution such that a center of mass of the drive assembly 172 is offset from the axis C. Such an asymmetrical weight distribution can be achieved, for example, by adding a structural element such as a ballast or other mass M, which may be integrally formed with or separately coupled to the housing 176. Alternatively, the asymmetric weight distribution could be achieved by a particular arrangement of multiple components of the drive assembly 172. For example, various components of the drive assembly 172, e.g., the drive assembly housing 176 and motor 180, can be weighted or arranged to provide the aforementioned asymmetrical weight distribution.

To turn the drive assembly 172, in one aspect the operator console 163 signals that one or more of the jacks 162 (see FIG. 2 and FIG. 3) be actuated to advance downward and push against the floor G, thereby raising at least the portion of the table base body 155 that is directly above the jack 162. This continues until the wheel 178 of the drive assembly 172 becomes suspended above the floor G, or there is insufficient friction between the drive assembly 172 and the floor G such that the drive assembly 172 can start to rotate simply due to gravity acting upon the asymmetric weight distribution (while there may still be some contact with the floor G in such an arrangement.) In this manner, upon lifting of one or more portions of the base body 155 by a respective jack 162, the weight of the mass M causes the drive assembly 172 to rotate (since the drive assembly 172 is free to rotate about its axis C by virtue of the bearing 174) under the influence of gravity, which positions the mass M as close as possible to the floor G. In this regard, the one or more jacks 162 can be selectively actuated to cause a desired reorientation of the drive assembly 172 with respect to the base body 155 of the table 5, and as a direct result the drive wheel 178 rotates (as one with the drive assembly housing 176) to a selected orientation. For example, in the arrangement of four jacks 162 positioned near respective corners of the base body 155, an operator at the operator console 163 can signal actuation of one or more jacks 162 to lift their corresponding portions of the base body 155 which results in the drive assembly 172 rotating to position the mass M furthest away from the actuated jacks 162, under the influence of gravity.

In another aspect, a plurality of actuators 161 (see also FIG. 2 and FIG. 3) are coupled to drive the plurality of casters 164, respectively so that one or more of the plurality of casters advances with respect to the body of the base thereby raising the first drive wheel off the floor.

Once a selected arrangement or sequence of actuation of the jacks 162, or of the actuators 161, has been received from the operator console 163 and which results in a desired orientation of the drive assembly 172, the operator console 163 signals the selected jacks 162 to retract until they are no longer in contact with the floor G, or the selected actuators 161 to retract their casters 164, and as a result the wheel 178 is lowered back down to rest in full contact with the floor G. Now however, the wheel 178 is in the desired orientation with respect to the center axis C. Next, the operator console 163 signals the motor 180 to drive the wheel 178 which in turn causes the table 5 to turn towards a direction defined by the plane of the wheel 178. In this regard, the drive motor 180 can be signaled from the operator console 163 to exert a torque on the table 100 to turn the table 100 toward a desired direction. If done from rest, this action releases the table 5 by flipping one or more of the casters 164 (the caster 164 swivels to point to the desired direction) which reduces the force needed from an operator to manually re-orient the table 5 toward a desired direction of motion and overcome caster flip, as described above.

Figure 7:
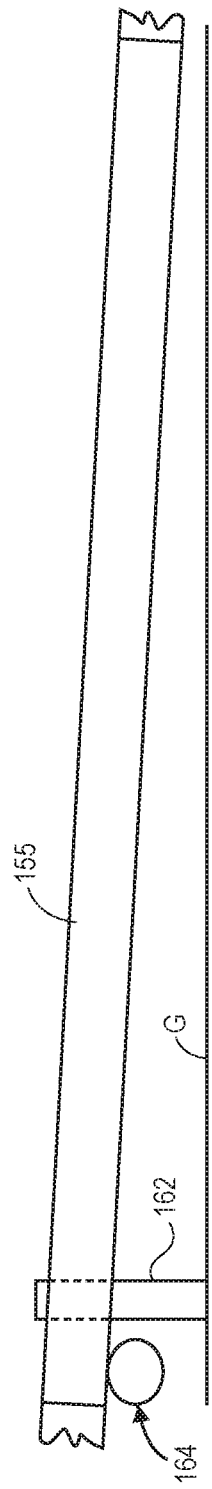

It should be noted that the aforementioned lifting of one or more portions of the base body 155 by selected jacks 162 may also have the effect of freeing respective casters 164 from friction against the floor G, enabling them to swivel freely about and therefore change orientation about their respective axes A (due to the inherent asymmetric distribution of weight in a caster.) This is depicted in the example shown in FIG. 7, in which a portion of the base body 155 is devoid of the drive assembly 172, and the jack 162 has advanced enough so as to lift that portion of the base body 155 so that the adjacent caster 164 becomes suspended above the floor G. This tilts the base upward in the direction of the raised caster in response to which the caster swivels due to gravity into a different orientation. Thereafter, the controllable jacks 162 can be signaled to retract so that the selected caster 164 (and its caster wheel 170) is lowered back down against the floor G but is now in a different orientation. The table 5 can now be pushed, pulled, or driven in that orientation (the desired direction of motion) more easily, in that less force is needed from the operator to manually re-orient the table 5 as described above.

Thus, in one aspect, in response to detecting an indication to move the table 5 in a desired direction or turn the table 5 to a desired direction, the programmed processor selects one or more of the jacks to advance with respect to the body of the base until the jack is pushing against the floor and thereby tilting the base upward in the desired direction. At that point, the raised caster is off the floor in response to which the caster swivels due to gravity to the desired direction.

In another aspect of the disclosure, as shown in FIG. 8, one or more of the casters 164 can be provided with a motor 180 that is mechanically coupled to a respective caster wheel 170 via a respective mechanical transmission 179, to drive the caster wheel 170 along the floor G (or horizontally.) Such a motorized caster 164 can be signaled from the operator console 163 to drive the caster wheel 170 to thereby move (drive) the table 5 forward or backward. More specifically, the motor 180 is activated to rotate its output shaft which imparts a torque to the respective caster wheel 170 via the mechanical transmission 179 such that the respective caster wheel 170 grips the floor G and rolls forwardly to linearly drive the table 5 along the floor G. This may be in addition to or an alternative to the assistance provided by the drive assembly 172 described above. In an arrangement in which four casters 164 are provided near opposing corners of the table base 150 as shown in FIG. 3, only two of the casters 164 that are diagonally opposite each other may be motorized (the other two may be passive.) In another variation, every one of the four casters 164 is provided with its respective motor 180. In such arrangements in which multiple casters 164 are motorized, a pair of diagonal casters 164 can be differentially driven by their respective motors 180 to affect directional control or turning of the table 5, e.g., by producing differential and spaced apart forces on the table base 150 that produce torques about the Z-axis.

Figure 9:
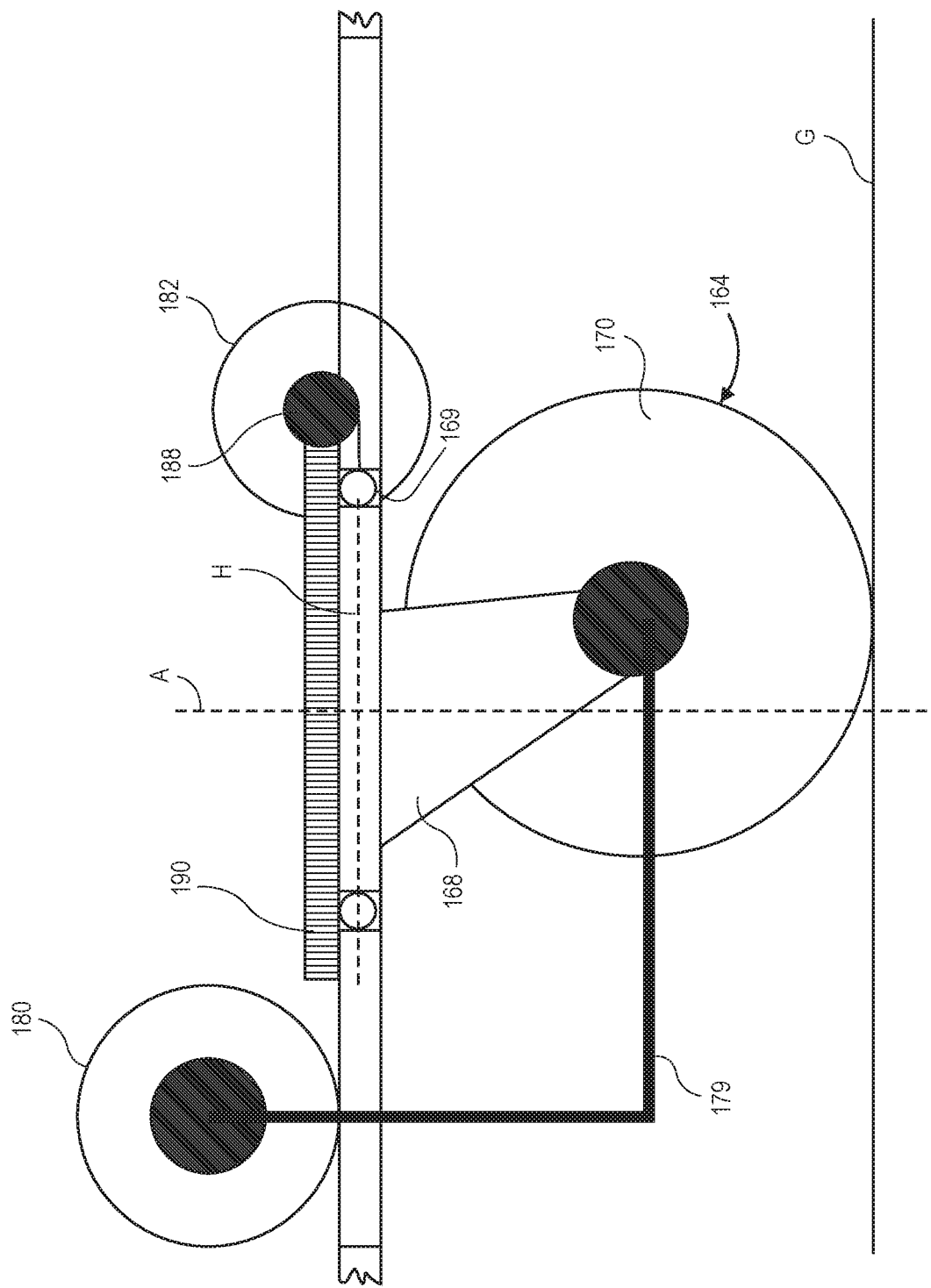

In another variation, as shown in FIG. 9, one or more of the casters 164 can be mechanically coupled to both a drive motor 180 and a rotation motor 182. The rotation motor 182 can be signaled from the operator console 163 to rotate the frame 168 to which the caster wheel 170 is mounted, about the axis A toward a desired direction of motion for the table 5. In the illustrated example, the output shaft of the rotation motor 182 can drive a worm gear 188 to turn, with the worm gear 188 positioned to mesh with and drive a spur gear 190 or other gear that is engaged with the caster wheel frame 168, to rotate the frame 168 along the bearing 169 and about the axis A. The axis A is perpendicular to a plane H in which lie the roller elements of the bearing 169 as shown. In addition, the drive motor 180, which is in mechanical communication to drive the caster wheel 170 via a respective mechanical transmission 179, can be signaled from the operator console 163 to impart rotational motion that drives the caster wheel 170 and therefore the table 5 in the direction to which the caster wheel 170 is pointing.

In one variation, a force/torque (F/T) sensor can be fitted to the caster 164 to sense the forces and torques that are being applied to the caster 164. For example, if an operator were to apply a turning force to the table 5, e.g., a force other than forward or backward along the longitudinal axis of the table 5, a torque would be produced on a respective caster 164 due to the caster wheel 170 being offset from the axis A as shown in the figures. The F/T sensor would sense this torque and provide a torque reading of it to a processor which in response signals the rotation motor 182 to produce a torque on the caster 164 that attempts to rotate the caster 164 about the A axis and that is proportional to the force/torque sensed by the sensor. The application of this torque upon the caster 164 may assist that which is being applied "manually" by a hand or foot of the operator, to make it easier for the operator to turn the table 5.

Figure 10:
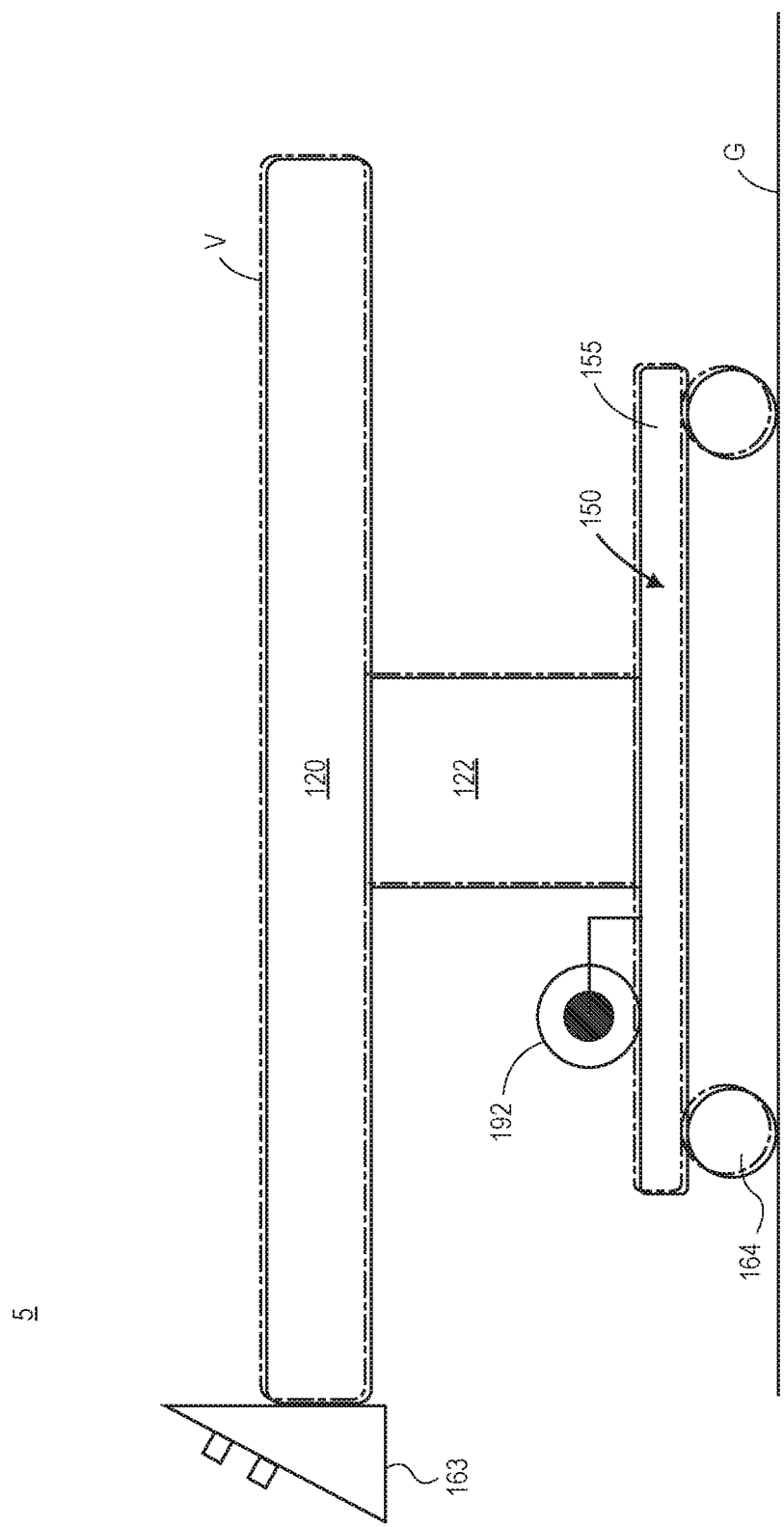

Turning to FIG. 10, this figure illustrates yet another aspect of the disclosure, in which a vibration motor 192 is mounted to the base body 155 and is configured to produce vibrations V in one or more portions of the table 5. The vibration motor 192 can be provided with an unbalanced or asymmetrical mass so as to produce periodic forces that produce vibrations V in one or more portions of the surgical table 5. In one variation, the vibrations V can be produced by surgical equipment of the surgical system 1 that is mounted or coupled to the surgical table 5, for example, by joint motors in the robotic arms 4 or their associated mounts. The vibration motor 192 can be signaled from the operator console 163 to induce a cross-talk effect by producing a force that induces a vibration at other portions of the table 5. Such vibrations can induce one or more of the casters 164 to oscillate so as to momentarily and intermittently alternate between contact with the floor G and minimized contact with, or suspension above, the floor G. It is easier for the operator (less manual force needed by the operator) to turn the table 5 during periods of such oscillations in which the respective casters 164 are in minimal contact with or free from contact with the floor G. During such periods, the operator is thus provided with an opportunity during which minimal or no friction between a caster wheel 170 and the floor G is present, such that the operator can manually exert enough forces on the table 5 to turn the table 5 without meeting resistance from caster flip (at the respective vibrating caster 164.) Such vibration of one or more of the casters 164 under the influence of the vibration motor 192 allow the operator to not only roll the table 5 forward or rearward more easily (with less initial force), but also turn the table 5 with a lessened resistance from friction/caster flip. In one aspect, the programmed processor in the operator console activates the one or more motors in response to detecting an indication to move the table. The programmed processor can detect the indication to move the table by sensing a force that is being applied by an operator to the table, or in response to user's manipulation of one or more user control interface elements in the operator console.

Figure 11:
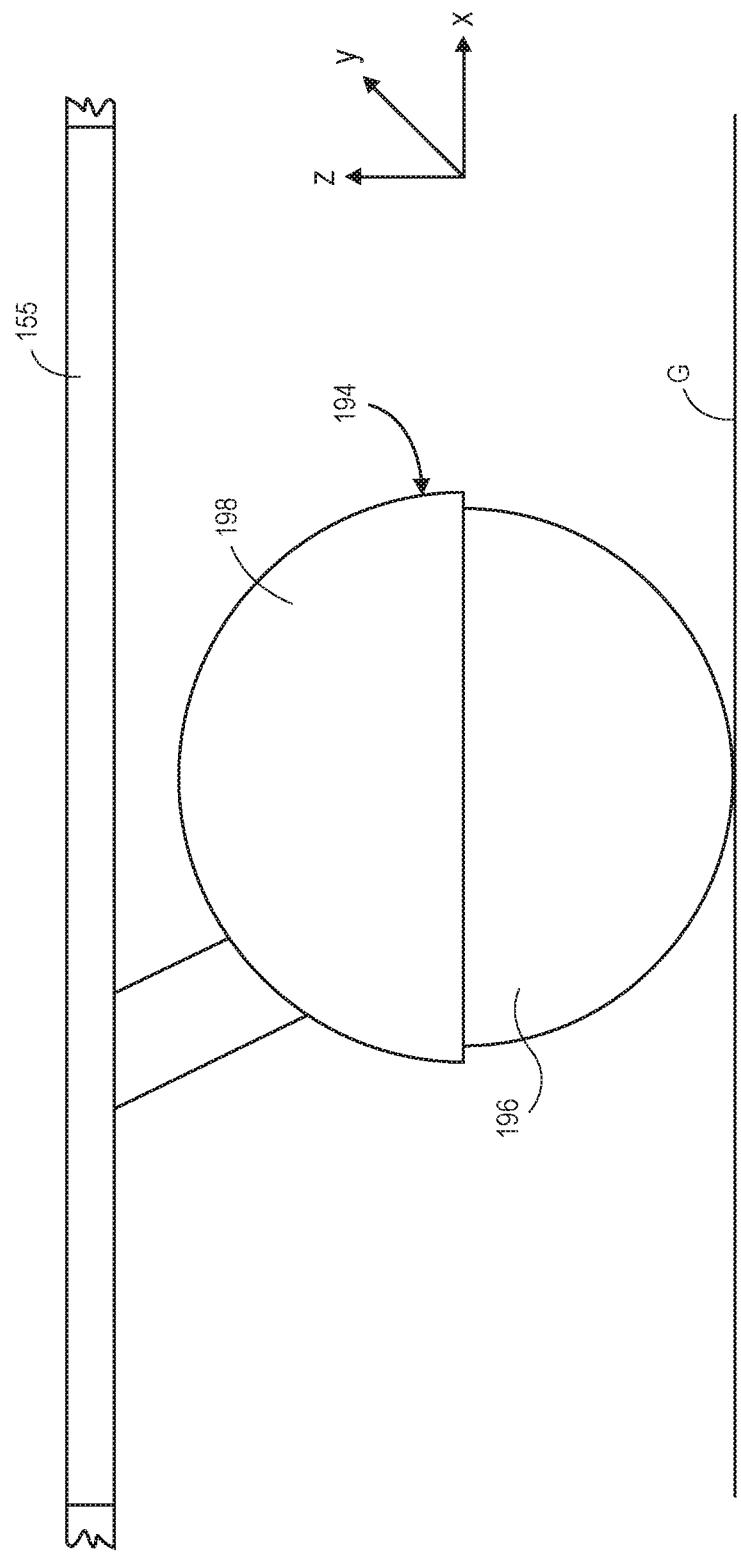

Turning to FIG. 11, in another aspect of the disclosure, the table base 150 can be provided with one or more special casters 194, wherein the forces and torques required to re-orient the caster 194 with respect to the base body 155 are minimized, inhibited or prevented. For example, the caster 194 can include a spherical member or spherical wheel 196 that is coupled to and at least partially retained with respect to a ring, cup, or frame 198, and the latter can be fixedly coupled to the base body 155, or it can be rotatably coupled to the base body 155 using the bearing 169 as described above for example in connection with FIG. 9. In this regard, the spherical wheel 196 is rotatable with respect to the frame 198 such that the spherical wheel 196 can rotate with regard to 3 rotational degrees of freedom, DOF, i.e., rotation about the X-axis, rotation about the Y-axis, and rotation about the Z-axis. This freedom to rotate may minimize the effect of caster flip when the operator is forcing the table 5 to turn. The spherical wheel 196 and the frame 198 can be selected with materials and surface configurations that provide minimal frictional engagement between each other, e.g., metallic materials and polymeric materials. In one embodiment, the spherical wheel 196 can be formed from a metallic material, and there may be several of such casters 194, e.g., five or more casters 194, mounted to the base body 155 as shown in FIG. 11. The table load is spread or distributed to all of the casters 194.

Figure 12:
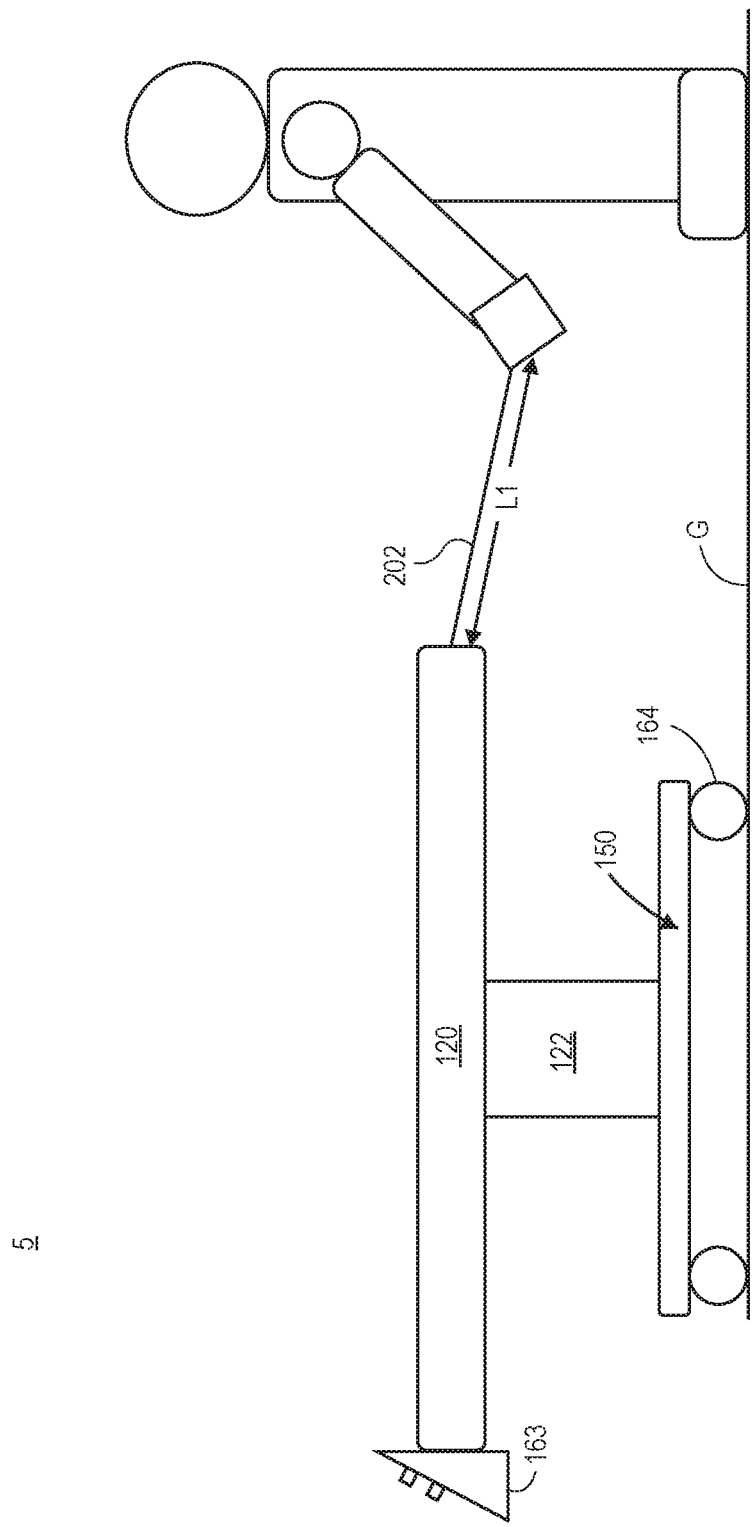
Figure 13:
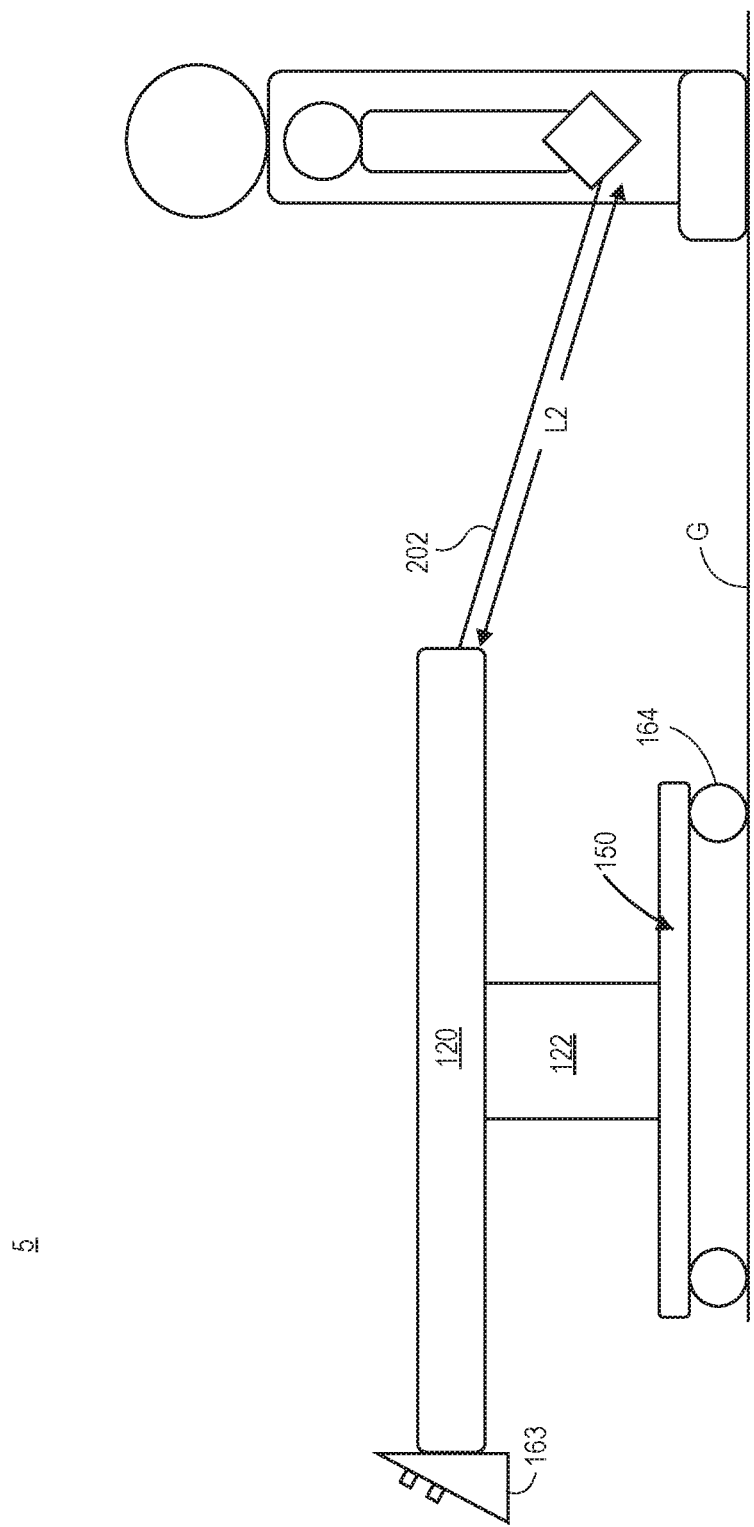

To change the momentum of the table 5 so as to make it easier to flip or turn the casters 164, for example when an operating is trying to turn the table, or even when the table 5 is to be driven forward or backward from rest, an impulse load can be applied to or exerted upon the table 5 manually by the operator. Several approaches are now described in which one or more manual actuators are provided on the table 5 that can store, amplify, or redirect a direct input force exerted by the operator, into the needed impulse load. For example, in one variation as shown in FIG. 12 and FIG. 13, the manual actuator is in the form of one or more kinematic members 202, e.g., kinematic straps or dynamic rope, that are coupled to the table 5 (e.g., the table top 120 as shown) such that an operator pulling on the kinematic members 202 will cause the table 5 to roll along the floor G on the casters 164, towards the operator. The kinematic members 202 are provided with elastic properties, e.g., are configured to elongate or stretch an amount proportional to an applied force by a predetermined or preselected constant value, so that they gradually stretch from a resting length L1 to a greater, stretched length L2 when pulled by the operator (see FIG. 12.) This stretching absorbs the energy associated with instantaneous sudden loads such that, upon an initial engagement and pulling of the kinematic members 202, the operator experiences a smooth, gradual force engagement to pull the table 5 in a desired direction of motion. Accordingly, the kinetic energy absorbing configuration of the kinematic members 202 is provided to protect the operator from sudden or jerking pulling motions that might increase the risk of injury due to strained muscles of the operator.

Furthermore, the kinetic energy absorbed by the kinematic members 202 upon stretching is stored as potential energy. The kinematic members 202 are thus biased to return toward a starting or resting configuration, by a force proportional to the distance stretched and the predetermined or preselected constant value. In this regard, the stored potential energy in the kinematic members 202 can further assist the operator's pulling force on the table 5. This assistance may be referred to as a biasing force that is produced, for example, upon the kinematic members 202 reaching their maximum or near-maximum stretched limit.

Figure 14:
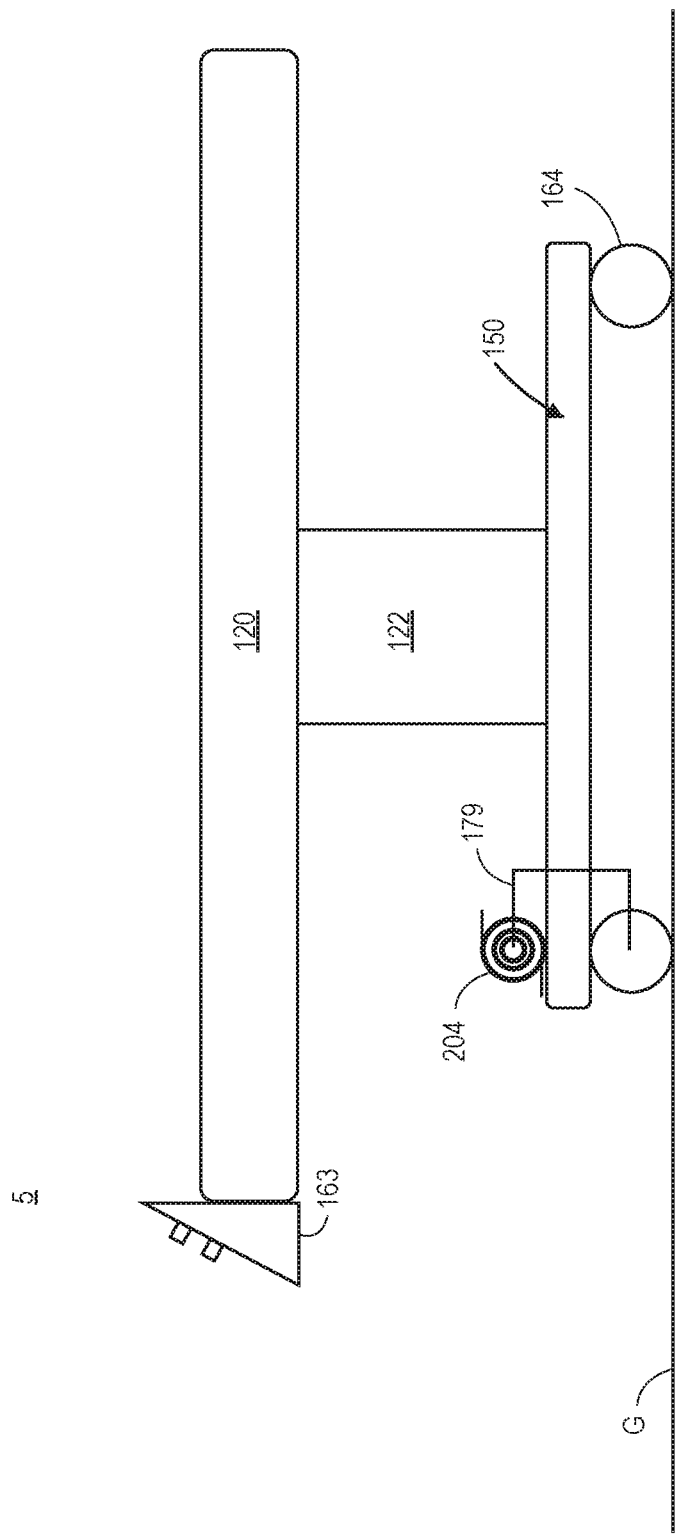
Figure 15:
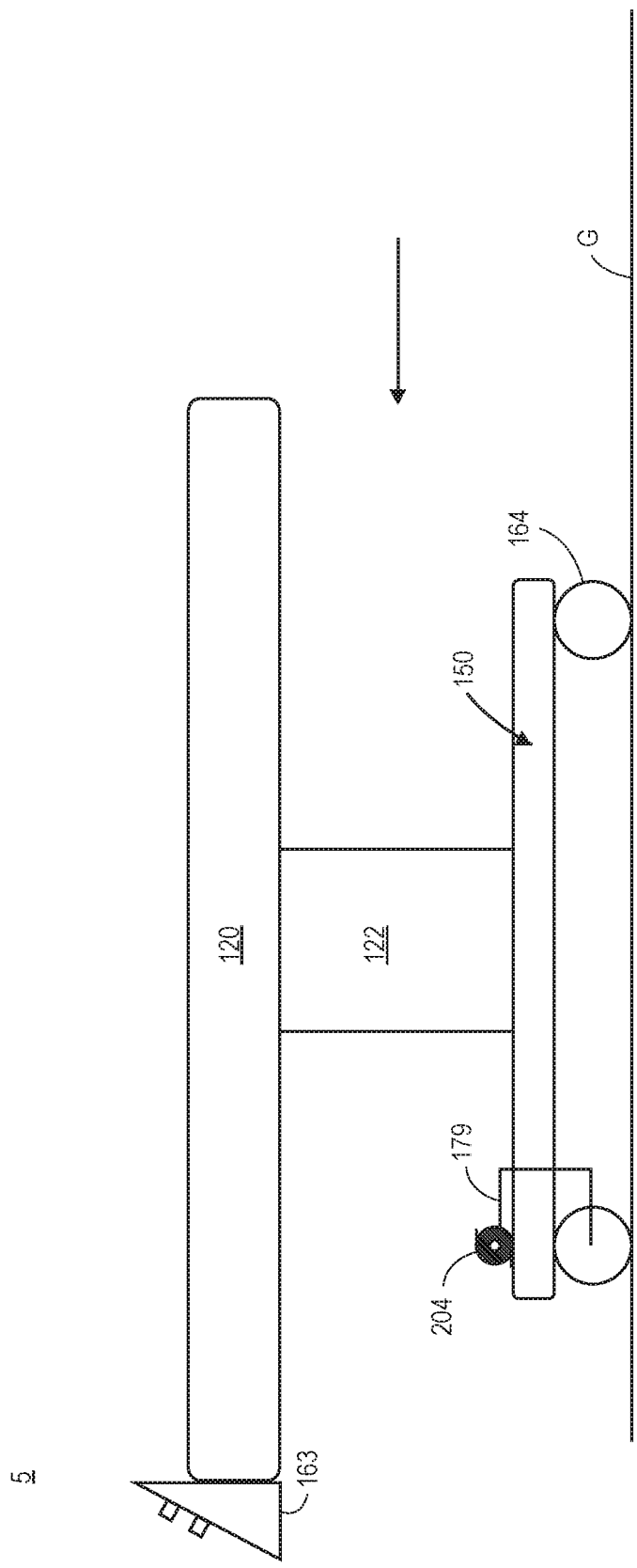

In another variation, as shown in FIG. 14 and FIG. 15, the mechanical actuator is in the form of a drive spring 204 that is in mechanical communication with one or more of the casters 164, either directly or via a mechanical transmission 179 as shown. The drive spring 204 can be a flexible body that twists and stores potential energy when acted upon by an applied torque. In this regard, the drive spring 204 can be a torsion spring formed from a helically wound metallic member that is biased to return toward a resting state when twisted or turned by an applied torque. The drive spring 204 can be wound or twisted into a compressed or torsion state, for example by the operator pulling or pushing the table 5 backwardly such that the caster wheel 170 (of the respective caster 164) rotates in one direction and thereby applies torque to wind the drive spring 204 (through the mechanical transmission 179.) The mechanical transmission 179 can then operate in reverse in response to the drive spring 204 unwinding into its resting state, which releases the stored potential energy by transferring torque to rotate the caster wheel 170 in an opposite direction. In variations, the drive spring 204 can be twisted in a different manner, for example, with a mechanical linkage such as a lever or crank that can be actuated by the operators hand or foot, or with an electric motor or generator. The spring 204 can be maintained in its torsion state, for example, by a brake, stop, ratchet and pawl, etc. that can then be released by the operator. Upon release of the drive spring 204 from its twisted configuration, the potential energy stored in the drive spring 204 in the twisted configuration is converted into rotational force and is applied to the mechanically coupled caster wheel 170 such that the untwisting of the drive spring 204 drives the caster wheel 170 to roll the table 5 forwardly or backwardly, depending on the arrangement of the mechanical transmission 179. In one variation, a mechanical transmission 179 can be selectively operated to exert clockwise or counter-clockwise torque on the caster wheel 170 to effect forward or backward rolling of the table 100.

Figure 16:
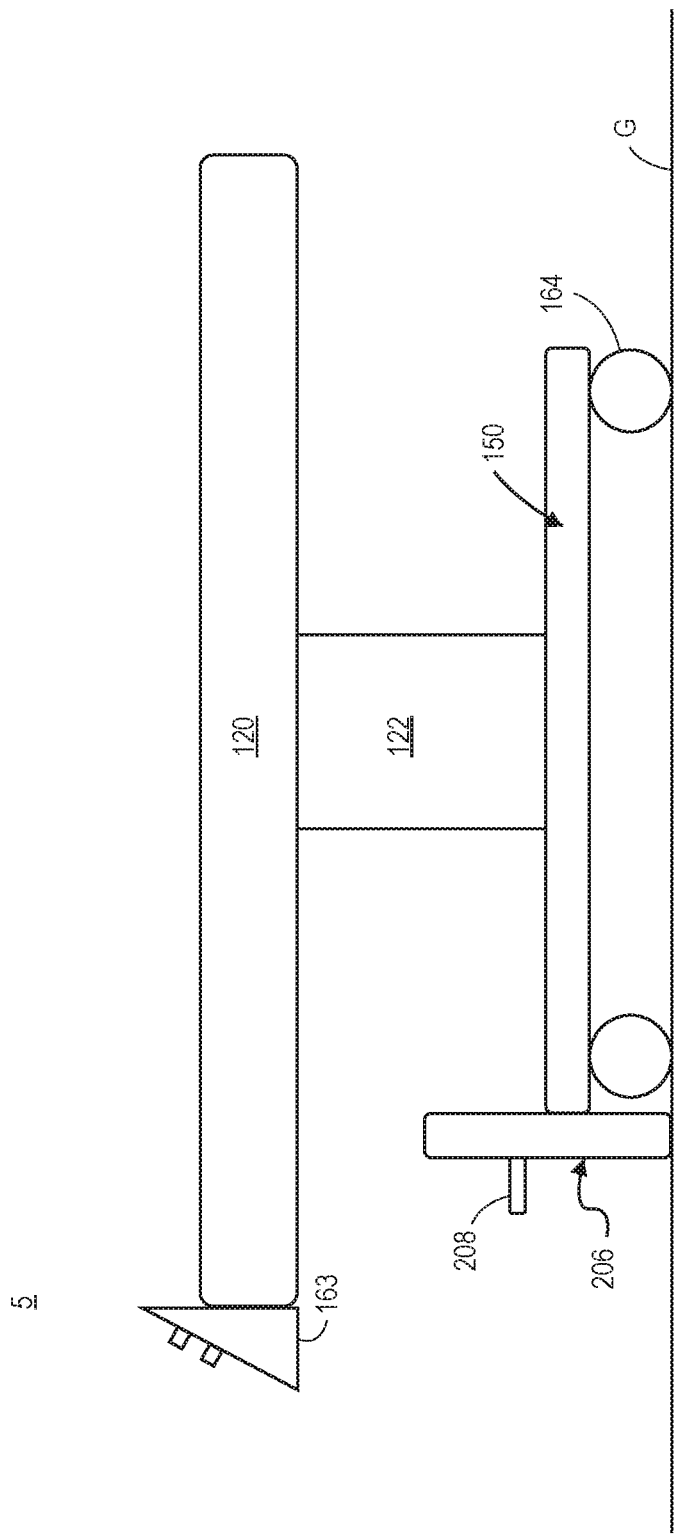
Figure 17:
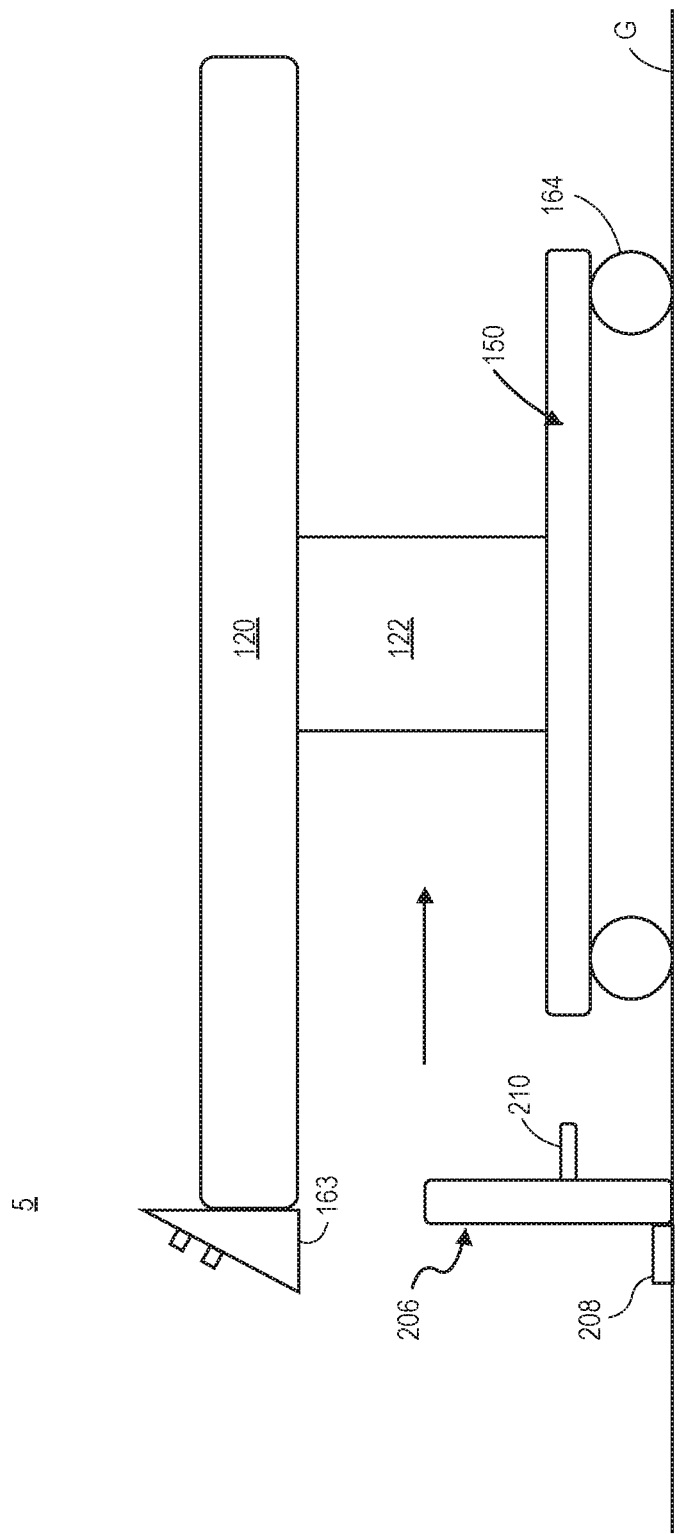

In still another variation of applying an impulse load to change the momentum of the table 5, as shown in FIG. 16 and FIG. 17, the mechanical actuator can be provided in the form of a drive station 206 that is in mechanical communication with the table 5. As shown, the drive station 206 can be a structure that is anchored to the floor G or another stationary element such as a wall, frame, etc., and includes a mechanical interface 208 that can engaged by for example a hand or a foot of the operator. The drive station 206 can be arranged such that upon application of an input force to the mechanical interface 208 by the operator, the drive station 206 transforms, e.g., amplifies or re-orients, the input force into an output force on the table base 150 that causes the table 5 to roll along the floor G on the casters 164. The mechanical interface 208 can be a crank, lever, pedal, etc., e.g., a foot pedal, that is coupled through a mechanical linkage, e.g., levers, gearing, drive chain, etc., to an output finger 210 (see FIG. 7) or other advancing output feature that is arranged to forcibly advance into engagement with the table 5. In one variation, the drive station 206 can include hydraulic components to amplify and reorient the input force provided by the operator. In another variation, the output feature of the drive station 206 can be a stream of compressed air or other fluid directed at a portion of the table 5. Accordingly, upon actuation of the drive station 206 via the mechanical interface 208, a redirected or amplified input force exerted by the output finger 210 on the table 5 causes the table to begin rolling on the casters 164 thereby reducing or obviating the need for the operator to directly supply the initial force needed to overcome the rolling resistance of the table 5.

The foregoing aspects of the disclosure provide surgical tables with configurations that assist or obviate the manual forces exerted by one or more operators on the table to overcome initial resistance to rolling or to overcome the effect of caster flip in reorienting the table. Such configurations can reduce the number of operators required to move the table in confined spaces such as a surgical operating room, and may even decrease the risk of injury to such operators, provide enhanced or fine control over the orientation and speed of the table, and improve overall efficiency. The surgical tables can thus be easily moved for example sideways for storage against a wall, and turned prior to, during, and following robotic surgery procedures in accordance with the foregoing, even when the table load includes the weight of heavy equipment such as robotic arms. Accordingly, surgical tables can be conveniently re-positioned in an operating environment as needed to suit the different requirements of a sequence of different surgical operations that are to be performed using the same table.

The following statements of invention can be made. 13) A surgical system, comprising: a surgical table for supporting a patient, the surgical table comprising a base and a table top supported on the base; a support assembly coupled to a body of the base and having a surface-engaging end in contact with a floor supporting the surgical table, the support assembly comprising a plurality of casters rotatably mounted to the body of the base; and a manual actuator coupled with the surgical table such that an input force applied to the manual actuator by an operator is converted to an impulse load that rolls the surgical table along the floor. 14) The surgical system of 13, wherein the manual actuator is one or more kinematic straps coupled to a portion of the table. 15) The surgical system of 14, wherein the one or more kinematic straps are configured to elongate from a first length to a second, longer length upon application of the input force by the operator. 16) The surgical system of 13, wherein the manual actuator is a drive spring in mechanical communication with one or more casters of the plurality of casters. 17) The surgical system of 16, wherein the drive spring is a torsion spring that can be twisted from a resting configuration to store potential energy, and the drive spring is biased toward the resting configuration to provide a torque to the one or more casters to roll the table along the floor. 18) The surgical system of 13, wherein the manual actuator comprises a drive station in mechanical communication with a portion of the surgical table. 19) The surgical system of 18, wherein the drive station comprises a mechanical input interface operably coupled to an extensible output actuator that imparts the impulse load to the table to roll the table across the floor. 20) The surgical table of 19, wherein the drive station is anchored to the floor.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical robotics table, comprising:
a base;
a support extending upwardly from the base; and
a table top on the support, wherein the table top is configured to support a patient,
wherein the base comprises
a body,
a plurality of casters mounted to the body of the base, wherein each of the casters is configured to rotate freely about a vertical axis of the caster, and
a drive assembly coupled to the body of the base, the drive assembly comprising
a housing mounted to the body of the base and configured to rotate relative to the body about a vertical axis of the drive assembly,
a first drive wheel configured to revolve with a rotating, horizontal first axle, wherein the first axle is mounted to the housing such that the first drive wheel is in contact with a horizontal floor when the casters are resting on, and supporting the base above, the floor,
a first electric drive motor in mechanical communication with the first axle to drive the axle and thereby drive the base along the floor, and
a second drive wheel configured to revolve with a rotating, horizontal second axle that is mounted to the housing such that the second drive wheel is in contact with the floor simultaneously with the first drive wheel,
wherein the drive assembly supports the first drive wheel and the second drive wheel such that the first drive wheel and the second drive wheel exert a torque on the housing to cause rotation thereof, relative to the body and about the vertical axis of the drive assembly while the first drive wheel and the second drive wheel are driven differentially.

2. The surgical robotics table of claim 1, wherein the housing of the drive assembly is configured to rotate freely about the vertical axis of the drive assembly, and wherein the housing and the first and second drive wheels rotate about the vertical axis of the drive assembly due to torque produced by the first drive wheel and the second drive wheel, revolving against the floor and about the first axle and the second axle, respectively, but in opposite directions.

3. The surgical robotics table of claim 2 wherein the drive assembly further comprises a second electric drive motor in mechanical communication with the second axle, wherein the first and second electric drive motors are to be activated to drive the first and second drive wheels to revolve in the same direction to thereby drive the base along the floor in a direction of the first and second drive wheels.

4. The surgical robotics table of claim 3 further comprising an operator console having a programmed processor that, in response to detecting an indication to move the table, signals the first and second electric drive motors to i) differentially drive the first and second drive wheels to thereby rotate the housing about the vertical axis of the drive assembly and then ii) drive the first and second drive wheels to revolve simultaneously in the same direction.

5. The surgical robotic table of claim 4 wherein the programmed processor of the operator console selects a table direction in accordance with the indication to move the table, and differentially drives the first and second drive wheels until the housing is rotated to match the selected table direction.

6. The surgical robotics table of claim 1 further comprising a second electric motor mounted to the body of the base and mechanically coupled to rotatably drive the housing with respect to the body of the base, about the vertical axis of the drive assembly.

7. The surgical robotics table of claim 6 further comprising an operator console having a programmed processor that, in response to detecting an indication to move the table, i) signals the second electric motor to drive and thereby rotate the housing about the vertical axis of the drive assembly and then ii) signals the first electric motor to drive the first drive wheel and thereby move the table which turns one or more of the casters.

8. The surgical robotics table of claim 7 wherein the programmed processor of the operator console selects a table direction in accordance with the indication to move the table, and signals the second electric motor to drive and thereby rotate the housing until the housing is rotated to match the selected table direction.

9. The surgical robotics table of claim 1 wherein the base further comprises a plurality of jacks each of which is controllable to advance with respect to the body of the base until the jack pushes against the floor and then continues to advance thereby raising the first drive wheel off the floor.

10. The surgical robotics table of claim 9, wherein the housing of the drive assembly is configured to rotate freely about the vertical axis of the drive assembly, and wherein the drive assembly is arranged with an asymmetrical weight distribution such that when the first drive wheel has been raised off the floor, the drive assembly housing rotates, with respect to the body of the base and due to gravity, to a different orientation.

11. The surgical robotic table of claim 10 further comprising an operator console having a programmed processor that, in response to detecting an indication to move the table, signals a selected one or more of the jacks to advance with respect to the body of the base until the jack is pushing against the floor and raising the first drive wheel off the floor which causes the housing to rotate about the vertical axis of the drive assembly to the different orientation.

12. The surgical robotics table of claim 1 wherein the base further comprises a plurality of actuators coupled to drive the plurality of casters and mounted to the body of the base, wherein each of the actuators is controllable to advance a respective, coupled caster with respect to the body of the base thereby tilting the base and raising the first drive wheel off the floor.

13. The surgical robotics table of claim 12 wherein the housing of the drive assembly is configured to rotate freely about the vertical axis of the drive assembly, and wherein the drive assembly is arranged with an asymmetrical weight distribution such that when the first drive wheel has been raised off the floor, the drive assembly housing rotates, with respect to the body of the base and due to gravity, to a different orientation.

14. The surgical robotics table of claim 1 wherein a force of at least 500 Newtons is needed to begin rolling the table or changing its direction.

15. The surgical robotics table of claim 1 wherein a total load of the table and a patient on the table is from 800 kg to 1000 kg.

16. The surgical robotic table of claim 1 wherein the plurality of casters are four casters.

17. A surgical robotics table, comprising:
a base having a plurality of jacks;
a support extending upwardly from the base; and
a table top on the support, wherein the table top is configured to support a patient,
wherein the base comprises
  a body,
  a plurality of casters mounted to the body of the base, and
  a drive assembly coupled to the body of the base, the drive assembly comprising
    a housing mounted to the body of the base and configured to rotate about a vertical axis of the drive assembly,
    a first drive wheel configured to revolve with a rotating, horizontal first axle, wherein the first axle is mounted to the housing such that the first drive wheel is in contact with a floor when the casters are resting on, and supporting the base above, the floor, and
    a first electric drive motor in mechanical communication with the first axle to drive the axle and thereby drive the base along the floor; and
  an operator console having a programmed processor that, in response to detecting an indication to move the table, signals a selected one or more of the plurality of jacks to advance until the selected jack is pushing against the floor and raising the first drive wheel off the floor which causes the housing to rotate about the vertical axis of the drive assembly to a different orientation, wherein the programmed processor then signals the selected one or more of the jacks to retract which lowers the first drive wheel back onto the floor, and then signals the first electric motor to drive the first drive wheel which grips the floor and thereby drives the table which turns one or more of the casters towards the different orientation.

18. A surgical robotics table, comprising:
a base having a plurality of actuators;
a support extending upwardly from the base; and
a table top on the support, wherein the table top is configured to support a patient,
wherein the base comprises
  a body,
  a plurality of casters mounted to the body of the base, and
  a drive assembly coupled to the body of the base, the drive assembly comprising
    a housing mounted to the body of the base and configured to rotate about a vertical axis of the drive assembly,
    a first drive wheel configured to revolve with a rotating, horizontal first axle, wherein the first axle is mounted to the housing such that the first drive wheel is in contact with a floor when the casters are resting on, and supporting the base above, the floor, and
    a first electric drive motor in mechanical communication with the first axle to drive the axle and thereby drive the base along the floor,
  wherein each of the plurality of actuators is controllable to advance a respective, coupled caster thereby tilting the base and raising the first drive wheel off the floor,
  the housing of the drive assembly is configured to rotate freely about the vertical axis of the drive assembly, and the drive assembly is arranged with an asymmetrical weight distribution such that when the first drive wheel has been raised off the floor, the drive assembly housing rotates, with respect to the body of the base and due to gravity, to a different orientation, and
  when the first drive wheel is raised off the floor, one of the casters is also raised off the floor and becomes free to rotate toward the different orientation.

* * * * *